US008855739B2

(12) United States Patent
Nagata et al.

(10) Patent No.: US 8,855,739 B2
(45) Date of Patent: Oct. 7, 2014

(54) ULTRASOUND EXAMINATION APPARATUS AND ULTRASOUND EXAMINATION METHOD USING LASER LIGHT TO DETECT MICROSCOPIC DISPLACEMENT CAUSED BY REFLECTED ULTRASONIC WAVES

(75) Inventors: Takayuki Nagata, Osaka (JP); Shinichi Kadowaki, Fukuoka (JP)

(73) Assignee: Panasonic Corporation, Osaka (JP)

( * ) Notice: Subject to any disclaimer, the term of this patent is extended or adjusted under 35 U.S.C. 154(b) by 57 days.

(21) Appl. No.: 13/523,930

(22) Filed: Jun. 15, 2012

(65) Prior Publication Data

US 2012/0253196 A1 Oct. 4, 2012

Related U.S. Application Data

(63) Continuation of application No. PCT/JP2011/005677, filed on Oct. 11, 2011.

(30) Foreign Application Priority Data

Oct. 21, 2010 (JP) .................................. 2010-236169

(51) Int. Cl.
*A61B 5/05* (2006.01)
*A61B 5/00* (2006.01)
*A61B 8/00* (2006.01)
*A61B 8/08* (2006.01)
*A61B 8/14* (2006.01)

(52) U.S. Cl.
CPC ................. *A61B 8/14* (2013.01); *A61B 5/0091* (2013.01); *A61B 8/4218* (2013.01); *A61B 8/0825* (2013.01); *A61B 8/4245* (2013.01); *A61B 5/0064* (2013.01); *A61B 8/0841* (2013.01); *A61B 5/0059* (2013.01); *A61B 8/5292* (2013.01)
USPC ........................... 600/407; 600/437; 600/476

(58) Field of Classification Search
USPC .......................................... 600/407, 437, 476
See application file for complete search history.

(56) References Cited

U.S. PATENT DOCUMENTS 5,309,907 A * 5/1994 Fang et al. ..................... 600/342
6,122,538 A * 9/2000 Sliwa et al. .................... 600/407

(Continued)

FOREIGN PATENT DOCUMENTS

CN 101420906 4/2009
CN 101431942 5/2009

(Continued)

OTHER PUBLICATIONS

International Search Report issued Nov. 29, 2011 in International (PCT) Application No. PCT/JP2011/005677.

(Continued)

*Primary Examiner* — Jonathan Cwern
*Assistant Examiner* — Amelie R Gillman
(74) *Attorney, Agent, or Firm* — Wenderoth, Lind & Ponack, L.L.P.

(57) ABSTRACT

The ultrasound examination apparatus according to an exemplary embodiment of the present disclosure is an ultrasound examination apparatus for observing an inside of a body of a living subject and includes: a transmitting probe that transmits ultrasonic waves to an inside of an examination target which is a part of the living subject; a receiving probe that detects microscopic displacement on a surface of the examination target without contact with the examination target, to detect reflected ultrasonic waves which are the to ultrasonic waves reflected from the inside of the examination target; and a signal processing unit that generates an image of the inside of the examination target, based on the reflected ultrasonic waves during a scanning operation in which the transmitting probe is kept fixed with respect to the examination target and the receiving probe is moved with respect to the examination target.

15 Claims, 10 Drawing Sheets

(56) References Cited

U.S. PATENT DOCUMENTS

| | | | |
|---|---|---|---|
| 6,245,015 B1* | 6/2001 | Pattanayak | 600/438 |
| 7,312,879 B2 | 12/2007 | Johnston | |
| 8,172,754 B2 | 5/2012 | Watanabe et al. | |
| 2005/0256404 A1* | 11/2005 | Sato | 600/437 |
| 2007/0081168 A1* | 4/2007 | Johnston | 356/614 |
| 2007/0187632 A1 | 8/2007 | Igarashi | |
| 2007/0197874 A1* | 8/2007 | Ishihara | 600/160 |
| 2007/0239020 A1 | 10/2007 | Iinuma et al. | |
| 2009/0163811 A1 | 6/2009 | Fukumoto et al. | |
| 2009/0198128 A1 | 8/2009 | Fukutani et al. | |
| 2009/0275834 A1 | 11/2009 | Watanabe et al. | |
| 2010/0228238 A1* | 9/2010 | Brennan et al. | 606/13 |
| 2010/0249570 A1* | 9/2010 | Carson et al. | 600/407 |
| 2011/0125004 A1* | 5/2011 | Thumma et al. | 600/407 |

FOREIGN PATENT DOCUMENTS

| | | |
|---|---|---|
| JP | 60-13109 | 1/1985 |
| JP | 05-056967 | 3/1993 |
| JP | 2002-228639 | 8/2002 |
| JP | 2003-310614 | 11/2003 |
| JP | 2003-329652 | 11/2003 |
| JP | 2007-216003 | 8/2007 |
| JP | 2007-301070 | 11/2007 |
| JP | 2008-170363 | 7/2008 |
| JP | 2009-090074 | 4/2009 |
| JP | 2009-225904 | 10/2009 |
| WO | 2010/013184 | 2/2010 |

OTHER PUBLICATIONS

Chinese Office Action issued Jul. 11, 2014 in corresponding Chinese Patent Application No. 201180005008.1 with partial English translation.

* cited by examiner

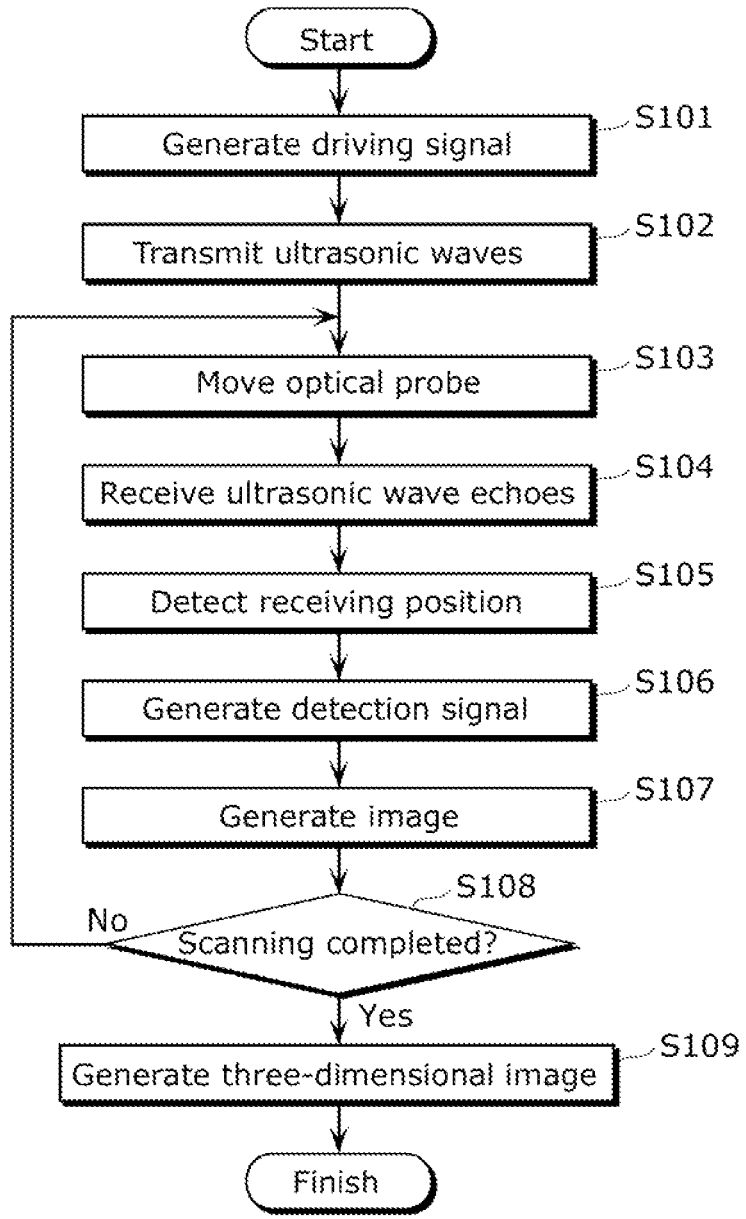

ULTRASOUND EXAMINATION APPARATUS AND ULTRASOUND EXAMINATION METHOD USING LASER LIGHT TO DETECT MICROSCOPIC DISPLACEMENT CAUSED BY REFLECTED ULTRASONIC WAVES

CROSS REFERENCE TO RELATED APPLICATIONS

This is a continuation application of PCT Patent Application No. PCT/JP2011/005677 filed on Oct. 11, 2011, designating the United States of America, which is based on and claims priority of Japanese Patent Application No. 2010-236169 filed on Oct. 21, 2010. The entire disclosures of the above-identified applications, including the specifications, drawings and claims are incorporated herein by reference in their entirety.

TECHNICAL FIELD

Apparatuses and methods consistent with one or more exemplary embodiments of the present disclosure relate to ultrasound examination apparatuses and ultrasound examination methods for observing an inside of a body of a living subject.

BACKGROUND ART

Development is ongoing for various types of techniques for supporting mass health examinations primarily aimed at early discovery of breast cancer. One of these is mammography screening which utilizes a breast imaging technique using X-ray. However, in mammography screening, when imaging of a breast having high tissue density is performed using X-ray, there is a possibility that accurate rendering of a lesion area is not possible, such as when the lesion is hidden in normal tissue, and so on. Furthermore, since imaging in mammography screening is performed with the breast being forcefully compressed vertically or horizontally, some subjects feel discomfort. As such, studies are being carried out on techniques for taking images of breasts using ultrasound in which the possibility of overlooking lesions is low and the burden on the subject is low.

CITATION LIST

Patent Literature

[PTL 1] Japanese Unexamined Patent Application Publication No. 2003-310614
[PTL 2] Japanese Unexamined Patent Application Publication No. 2007-301070

SUMMARY OF INVENTION

Technical Problem

However, there is a demand for further improvement of image quality in such an ultrasound examination apparatus.

One or more exemplary embodiments of the present disclosure solve the aforementioned conventional problems and provide an ultrasound examination apparatus capable of improving image quality. Additional benefits and/or advantages of the disclosed embodiments will be apparent from the specification and Figures. The benefits and/or advantages may be individually provided by the various embodiments and features of the specification and drawings of the disclosure, and need not all be provided in order to obtain one or more of the same.

Solution to Problem

In order to solve the aforementioned problems, the ultrasound examination apparatus according to an exemplary embodiment of the present disclosure is an ultrasound examination apparatus for observing an inside of a body of a living subject, the ultrasound examination apparatus including: a transmitting probe that transmits ultrasonic waves to an inside of an examination target which is a part of the living subject; a receiving probe that detects microscopic displacement on a surface of the examination target without contact with the examination target, to detect reflected ultrasonic waves which are the ultrasonic waves reflected from the inside of the examination target; and a signal processing unit configured to generate an image of the inside of the examination target, based on the reflected ultrasonic waves during a scanning operation in which the transmitting probe is kept fixed with respect to the examination target and the receiving probe is moved with respect to the examination target.

Advantageous Effects of Invention

Accordingly, one or more exemplary embodiments of the present disclosure provide an ultrasound examination apparatus capable of improving image quality.

BRIEF DESCRIPTION OF DRAWINGS

These and other advantages and features of exemplary embodiments of the present disclosure will become apparent from the following description thereof taken in conjunction with the accompanying Drawings that illustrate general and specific:exemplary embodiments of the present disclosure. In the Drawings:

FIG. 8 is a flowchart showing the operation of the ultrasound examination apparatus according to Embodiment 1 of the present disclosure;

Figure 1:
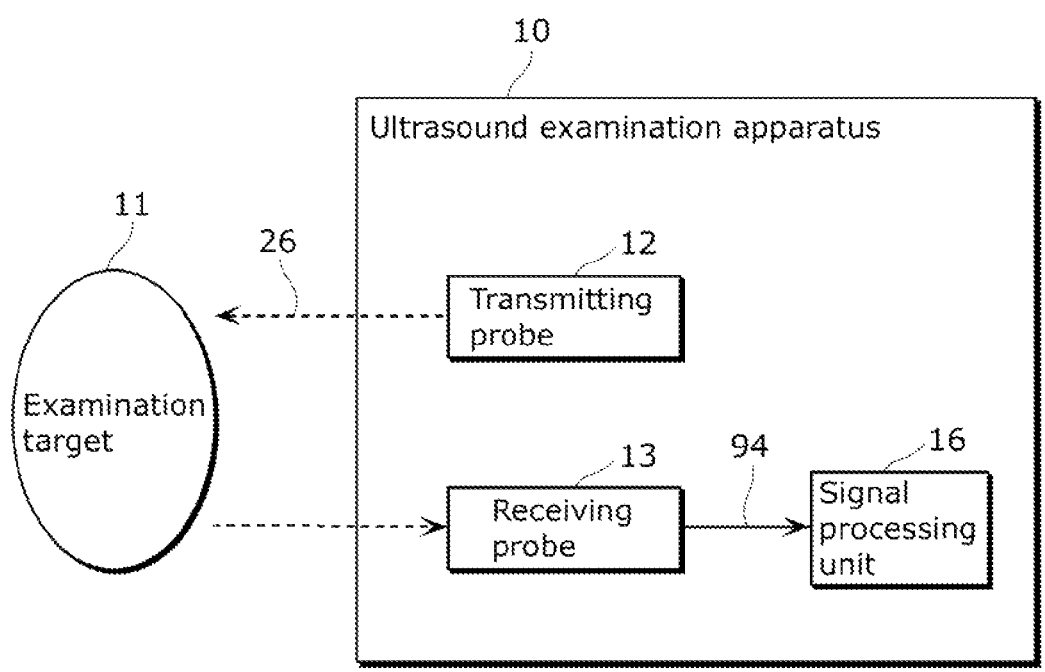
FIG. 1 is a block diagram showing the configuration of an ultrasound examination apparatus according to Embodiment 1 of the present disclosure.

DESCRIPTION OF EMBODIMENTS (Underlying Knowledge Forming Basis of the Present Disclosure)

The inventors have discovered that the conventional configurations have the problems described below.

An ultrasound examination apparatus is an apparatus that transmits ultrasonic waves to the inside of a part of a subject that is to be examined (hereafter referred to as an examination target) and performs imaging of information regarding the inside of the examination target based on reflected waves (hereafter referred to as ultrasonic wave echoes) that are reflected off of the interface of tissues (hereafter referred to as reflective tissues) inside the examination target that have different acoustic impedances. At present, when breast cancer diagnosis is performed using such an ultrasound examination apparatus, a technician manually moves an ultrasound probe (hereafter referred to as a probe). With this, the ultrasound examination apparatus displays a cross-sectional image (hereafter referred to as a tomographic image) of the breast. The technician examines the entire cross section of the breast while viewing the displayed cross-sectional images. Then, a tomographic image showing a possible abnormality is recorded, and a doctor subsequently interprets the recorded image and makes a diagnosis. However, in such a method, there are the problems of the diagnosis result being largely dependent on the proficiency of the technician, and of limited reproducibility of data. In addition, such a method has the problem of taking a long time to examine one person.

As such, recent years have seen the advancement of the development of an ultrasound examination apparatus which mechanically moves a probe to thereby take tomographic images of a breast, without dependency on the proficiency of a technician (for example, see PTL 1). In the method in PTL 1, the probe is brought into contact with the breast of a subject who is lying face-up, and ultrasound data is collected while the probe mechanically circles the breast with the nipple as a center. With this, tomographic images are taken in the above method. Such a method is called a direct-contact method.

On the other hand, there is a method called the immersion method in which ultrasonic waves are transmitted and received by providing warm water, and the like, between the probe and the breast. Although the immersion method makes it possible to take images of the entire breast almost in its natural shape, the immersion method has the problem that image quality deteriorates when the surface of the breast is tilted with respect to the ultrasonic wave transmission and reception directions. A technique described in PTL 2, for example, is a technique which uses the immersion method. With the ultrasound examination apparatus described in PTL 2, the position of the probe is adjusted according to the size of individual breasts in order to obtain images with minimal deterioration. Specifically, in the ultrasound examination apparatus described in PTL 2, pre-scanning is performed to measure the outer shape of the breast, and the tilt of the surface of the breast is calculated from the obtained outer shape data. In addition, the ultrasound examination apparatus attempts to transmit and receive ultrasonic waves perpendicularly with respect to the breast by tilting the probe to follow the tilt of the breast.

However, these conventional configurations have the problems described below.

In the configuration in PTL 1, tomographic images are taken by causing the probe to mechanically revolve while being in contact with the breast. However, since the breast consists of soft tissue, with this method, the shape of the breast changes significantly with every image-taking. Accordingly, each of the tomographic images taken becomes a tomographic image of a breast of a different shape. Therefore, when automatic examination is performed Using such method and a doctor carries out a diagnosis based on the examination result, it is necessary to interpret a large number of tomographic images of different shapes per image-taking. In other words, with the configuration in PTL 1, it is difficult to perform efficient diagnosis.

Here, in order to make a quick and detailed diagnosis using the large number of tomographic images taken, it is preferable that these tomographic images be converted into three-dimensional voxel data and recorded to allow display of arbitrary cross sections. However, as described above, with the technique in PTL 1, the ultrasound probe which transmits and receives ultrasonic waves needs to be moved while being pressed onto the examination target, and thus the shape of the examination target changes during the examination. As such, the state of change and the amount of deformation of the examination target are different per image-taking (depending on the time of the imaging). Furthermore, the effect of the deformation of the examination target is different for each of the tomographic images. As such, it is necessary to compensate for the deformation of the examination target for each of the tomographic images, and thus reconstruction of a three-dimensional image is difficult.

In addition, such direct-contact method has the problem of the likely emergence of a part at which the probe and the body surface do not touch due to breast shape and size differences between individuals. As such, it becomes difficult to transmit and receive ultrasonic waves accurately, and, as a result, image quality of the tomographic images deteriorates. Furthermore, since the deformation of the examination target is not reproducible, there is the problem that the images obtained lack reproducibility. Therefore, it cannot be considered to be sufficient as an automated examination apparatus which performs diagnosis automatically, without the judgment of an examiner.

On the other hand, with the immersion method described in PTL 2, the probe does not come into contact with the surface of the breast, and thus the shape of the breast does not change from the initial state and images with good reproducibility can always be obtained. Furthermore, countermeasures have been taken with regard to the angle of incidence of ultrasonic waves to the breast, which was a problem, and thus the method is considered to have certain advantageous effects. However, this attempt to prevent image quality deterioration cannot be considered sufficient. Specifically, the technique described in PTL 2 adjusts the tilt angle of the probe by considering that the tilt angles of the breast that is made to droop in a water tank are approximately uniform. Accordingly, when the tilt angles are different at the vicinity of the center and at the vicinity of the edge of the probe for example, there is a possibility that a tomographic image with sufficient image quality cannot be obtained for a part of a region in which scanning is performed.

One or more exemplary embodiments of the present disclosure is intended to solve the aforementioned conventional problems and provide an ultrasound examination apparatus capable of reducing the amount of deformation of an examination target during examination and improving image quality.

In order to solve the aforementioned problems, the ultrasound examination apparatus according to an exemplary embodiment of the present disclosure is an ultrasound examination apparatus for observing an inside of a body of a living subject, the ultrasound examination apparatus including: a transmitting probe that transmits ultrasonic waves to an inside of an examination target which is a part of the living subject; a receiving probe that detects microscopic displacement on a surface of the examination target without contact with the examination target, to detect reflected ultrasonic waves which are the ultrasonic waves reflected from the inside of the examination target; and a signal processing unit configured to generate an image of the inside of the examination target, based on the reflected ultrasonic waves during a scanning operation in which the transmitting probe is kept fixed with respect to the examination target and the receiving probe is moved with respect to the examination target.

With this configuration, the ultrasound examination apparatus according to an exemplary embodiment of the present disclosure generates an image based on the reflected ultrasonic waves when the non-contact receiving probe is moved in the state where the transmitting probe is kept fixed. With this, the amount of deformation of the examination target during examination can be reduced, and deterioration of image quality can be suppressed because the surface of the examination target and the probe do not come into contact. In addition, the ultrasound examination apparatus detects the reflected ultrasonic waves by detecting the microscopic displacement on the surface of the examination target. With this, the ultrasound examination apparatus can generate excellent images whose image quality has little dependency on the tilt angle of the surface of the examination target. Accordingly, the ultrasound examination apparatus according to an exemplary embodiment of the present disclosure is capable of reducing the amount deformation of an examination target during examination and improving image quality.

Furthermore, the receiving probe may include: a first light source that emits a laser light; a splitting element that splits the laser light into a detection light and a reference light; an irradiating optical system that irradiates the examination target with the detection light to form a light spot on the surface of the examination target; a light-receiving element that receives an interfering light of the reference light and a reflected detection light which is the detection light reflected off of the light spot, and generates a beat signal that is in accordance with the interfering light; and a receiving unit configured to FM-demodulate the beat signal to generate a detection signal indicating the microscopic displacement on the surface of the examination target at the light spot.

According to this configuration, the ultrasound examination apparatus according to an exemplary embodiment of the present disclosure can detect reflected ultrasonic waves without contact with the examination target.

Furthermore, the ultrasound examination apparatus may further include a position detecting unit configured to calculate a first relative positional relationship between the light spot and the receiving probe, based on a frequency of the beat signal.

According to this configuration, the ultrasound examination apparatus according to an exemplary embodiment of the present disclosure can detect the relative positional relationship between the light spot and the receiving probe.

Furthermore, the position detecting unit may be further configured to: detect a second relative positional relationship between the transmitting probe and the receiving probe; and calculate a third relative positional relationship between the transmitting probe and the light spot, based on the first relative positional relationship and the second relative positional relationship, and the signal processing unit may be configured to generate the image by computing, based on the third relative positional relationship, a time it takes for the reflected ultrasonic waves to reach the light spot, and performing phase rectifying addition on the detection signal using the time.

According to this configuration, the ultrasound examination apparatus according to an exemplary embodiment of the present disclosure can generate an image of the inside of the examination target based on the detection signal.

Furthermore, the ultrasound examination apparatus may further include a driving unit configured to changeably fix a relative positional relationship and relative angle between the receiving probe and the transmitting probe, wherein the driving unit may be configured to perform the scanning operation by keeping the transmitting probe fixed with respect to the examination target and moving the receiving probe with respect to the examination target.

According to this configuration, the ultrasound examination apparatus according to an exemplary embodiment of the present disclosure can automatically move the receiving probe.

Furthermore, the ultrasound examination apparatus may further include a control unit configured to calculate a tilt angle formed, at the light spot, between the surface of the examination target and the receiving probe, and adjust an amplitude of the microscopic displacement detected at the light spot, according to the tilt angle.

According to this configuration, the ultrasound examination apparatus according to an exemplary embodiment of the present disclosure can suppress the deterioration of image quality in the case where the surface of the examination target is tilted with respect to the receiving probe.

Furthermore, the control unit may be configured to calculate the tilt angle by estimating a shape of the surface of the examination target using the first relative positional relationship.

According to this configuration, the ultrasound examination apparatus according to an exemplary embodiment of the present disclosure can calculate the tilt angle formed between the surface of the examination target and the receiving probe.

Furthermore, the first light source may emit the laser light having a sawtooth-modulated optical frequency.

Furthermore, the position detecting unit may be configured to: calculate a difference between an optical path of the detection light and an optical path of the reference light, based on the frequency of the beat signal; and calculate the first relative positional relationship based on an emission angle of the detection light and the optical path difference.

According to this configuration, the ultrasound examination apparatus according to an exemplary embodiment of the present disclosure can calculate the first relative positional relationship even when the angle of emission of the detection beam is not perpendicular.

Furthermore, the ultrasound examination apparatus may further include a driving unit configured to changeably fix a relative positional relationship and relative angle between the receiving probe and the transmitting probe, wherein the position detecting unit may be configured to detect the second relative positional relationship based on information outputted from the driving unit and indicating the relative positional relationship and relative angle between the receiving probe and the transmitting probe.

According to this configuration, the ultrasound examination apparatus according to an exemplary embodiment of the present disclosure can detect the relative positional relationship between the transmitting probe and the receiving probe.

Furthermore, one of the transmitting probe and the receiving probe may include a second light source, the other of the transmitting probe and the receiving probe may include an optical sensor that detects, using an image, a light from the second light source, and the position detecting unit may be configured to detect the second relative positional relationship, based on a relationship between plural positions of the second light source as seen from the optical sensor.

According to this configuration, the ultrasound examination apparatus according to an exemplary embodiment of the present disclosure can detect the relative positional relationship between the transmitting probe and the receiving probe, even in the case where the transmitting probe and the receiving probe are completely detached from each other. With this, for example, a technician can perform the examination while freely moving the receiving probe by hand.

Furthermore, the transmitting probe may include a first gyro-sensor that detects an orientation of the transmitting probe, the receiving probe may include a second gyro-sensor that detects an orientation of the receiving probe, and the position detecting unit may be configured to detect a relative angle formed between the transmitting probe and the receiving probe, by comparing the orientation of the transmitting probe detected by the first gyro-sensor and the orientation of the receiving probe detected by the second gyro-sensor.

According to this configuration, the ultrasound examination apparatus according to an exemplary embodiment of the present disclosure can detect the relative angle formed between the transmitting probe and the receiving probe, even in the case where the transmitting probe and the receiving probe are completely detached from each other.

Furthermore, the receiving probe may further include a display that displays a tomographic image of the inside of the examination target, and the display may display a tomographic image of a cross-section of the inside of the examination target which is approximately parallel to a display surface of the display.

This configuration makes it easier for the technician to intuitively judge the position of a tumor and so on. This facilitates, for example, the guiding of a needle to a suspected part in an examination such as a mammotome biopsy.

Furthermore, the transmitting probe may transmit the ultrasonic waves to the inside of the examination target, in a state where the transmitting probe is in contact with the examination target.

It should be noted that the present inventive concept can be implemented, not only as an ultrasound examination apparatus such as those described herein, but also as a method having, as steps, the characteristic processing units included in such image-capturing apparatus, or a program causing a computer to execute such characteristic steps. In addition, it goes without saying that such a program can be distributed via a non-transitory computer-readable recording medium such as a CD-ROM and via a transmitting medium such as the Internet.

Hereinafter, some exemplary embodiments shall be described with reference to the Drawings. It should be noted that the same reference signs are assigned to same components and there are cases where their description shall not be repeated. Furthermore, the figures primarily illustrate the respective constituent elements schematically in order to facilitate understanding, and thus the shapes, and so on, may not be displayed accurately.

Furthermore, each of the embodiments described below illustrate a general or specific example. The numerical values, shapes, materials, structural elements, the arrangement and connection of the structural elements, steps, the processing order of the steps etc. shown in the following exemplary embodiments are mere examples, and therefore do not limit the inventive concept, the scope of which is defined in the appended Claims and their equivalents. Therefore, among the structural elements in the following exemplary embodiments, structural elements not recited in any one of the independent claims defining the most generic part of the inventive concept are not necessarily required to overcome conventional disadvantages.

Embodiment 1

An ultrasound examination apparatus according to Embodiment 1 of the present disclosure includes a receiving probe which detects reflected ultrasonic waves, without contact with an examination target. In addition, the ultrasound examination apparatus causes the non-contact receiving probe to move, with a transmitting probe in a fixed (stationary) state with respect to the examination target Accordingly, the ultrasound examination apparatus is capable of providing an ultrasound examination apparatus capable of reducing the amount deformation of an examination target during examination and improving image quality.

First, the basic configuration of the ultrasound examination apparatus according to Embodiment 1 of the present disclosure shall be described.

FIG. 1 is a block diagram showing the outline configuration of an ultrasound examination apparatus 10 according to Embodiment 1 of the present disclosure.

The ultrasound examination apparatus 10 is an ultrasound examination apparatus for observing an inside of a body of a living subject. The ultrasound examination apparatus 10 includes a transmitting probe 12, a receiving probe 13, and a signal processing unit 16.

The transmitting probe 12 is an ultrasound probe which transmits ultrasonic waves 26 to the inside of an examination target 11 of the subject.

The receiving probe 13 detects reflected ultrasonic waves (also referred to as ultrasonic wave echoes) which are the ultrasonic waves 26 that are reflected back from inside the examination target 11, by detecting microscopic displacement on the surface of the examination target 11 without contact with the examination target 11, and generates a detection signal 94 that is in accordance with the reflected ultrasonic waves.

The signal processing unit 16 generates images of the inside of the examination target 11, based on the ultrasonic wave echoes during the scanning operation in which the transmitting probe 12 is kept fixed (stationary) with respect to the examination target 11, and the receiving probe 13 is moved with respect to the examination target 11.

Figure 2:
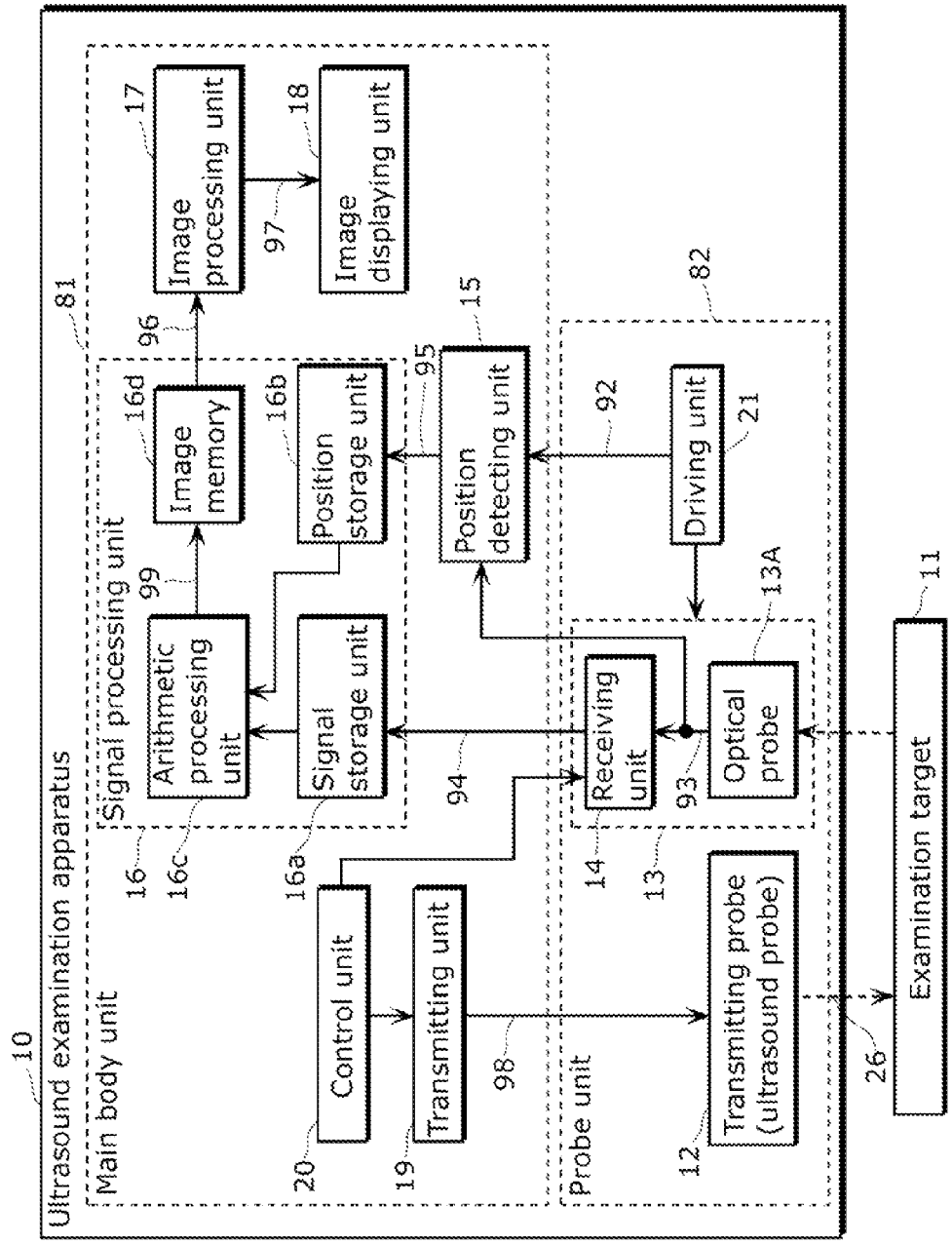
FIG. 2 is a block diagram showing the configuration of the ultrasound examination apparatus according to Embodiment 1 of the present disclosure.

FIG. 2 is a detailed block diagram of the ultrasound examination apparatus 10.

As shown in FIG. 2, the ultrasound examination apparatus 10 includes a main body unit 81 and a probe unit 82. It should be noted that the placement of the processing units shown in FIG. 2 is an example, and part of the processing units included in the main body unit 81 may be included in the probe unit 82, and part of the processing units included in the probe unit 82 may be included in the main body unit 81.

The probe unit 82 transmits the ultrasonic waves 26 to the examination target 11 and detects the ultrasonic wave echoes. Furthermore, the probe unit 82 outputs, to the main body unit 81, the detection signal 94 which is based on the detected ultrasonic wave echoes.

The probe unit 82 includes the transmitting probe 12, the receiving probe 13, and a driving unit 21. Furthermore, the receiving probe 13 includes an optical probe 13A and a receiving unit 14.

The optical probe 13A detects the shape and micro vibrations of the surface of the examination target 11 using light, modulates the detected information, and outputs a beat signal 93 obtained through the modulation.

The receiving unit 14 demodulates the beat signal 93 outputted from the receiving probe 13, and generates the detection signal 94 by performing amplification and digital conversion of the signal obtained through the demodulation.

The driving unit 21 mechanically connects the transmitting probe 12 and the receiving probe 13, and three-dimensionally moves the relative position of the receiving probe 13 with respect to the transmitting probe 12.

The main body unit 81 includes a position detecting unit 15, the signal processing unit 16, an image processing unit 17, an image displaying unit 18, a transmitting unit 19, and a control unit 20.

The position detecting unit 15 calculates the relative positional relationship between the transmitting position and the receiving position of the ultrasonic waves 26, using the beat signal 93 outputted from the optical probe 13 and positioning data 92 of the driving unit 21, and generates relative position information 95 indicating the calculated positional relationship.

The signal processing unit 16 generates three-dimensional data 96 by performing digital beam forming using the detection signal 94 generated by the receiving unit 14 and the relative position information 95 generated by the position detecting unit 15.

The image processing unit 17 generates a three-dimensional image 97 by performing three-dimensional image rendering and so on, based on the three-dimensional data 96 generated by the signal processing unit 16.

The image displaying unit 18 displays the three-dimensional image 97 generated by the image processing unit 17.

The transmitting unit 19 generates a driving signal 98 for transmitting the ultrasonic waves 26. The control unit 20 controls the transmitting unit 19 such that the driving signal 98 is generated at a predetermined timing.

Here, the transmitting probe 12 includes a transducer array in which plural transducers are two-dimensionally arranged. Each of the transducers includes a piezoelectric element made of a piezoelectric ceramic, and so on, represented by lead zirconate titanate (PZT), and an electrode connected to the piezoelectric element. In the transducer array, voltage in pulse-form sent from the transmitting unit 19 is applied to the electrode of each of the transducers to thereby generate ultrasonic wave pulses. Furthermore, the transmitting probe 12 can change the focus of the ultrasonic waves 26, and can deflect the ultrasonic waves 26. Furthermore, the pulse-form voltage has Undergone delay processing by the transmitting unit 19. With this configuration, the transmitting probe 12 can perform sector scanning in which the ultrasonic waves 26 are transmitted in three-dimensional directions.

Here, unlike in the conventional ultrasound examination apparatus, the optical probe 13A does not come into contact with the body surface of the examination target 11. In other words, a space of a predetermined distance exists between the bottom surface of the optical probe 13A and the examination target 11. This configuration reduces the deformation of the examination target 11.

Furthermore, the optical probe 13A splits a frequency-modulated laser beam into a detection beam and a reference beam, and forms plural light spots (hereafter referred to as receiving spots) on the surface of the examination target 11 using the detection beam. It should be noted that the detection beam is light that is emitted from the optical probe 13A towards the surface of the examination target 11. The reference beam refers to light that is reflected by a polarized-light reflecting plate 37 inside the optical probe 13A. Furthermore, the optical probe 13A detects the ultrasonic wave echoes by causing interference between the reference beam and the detection beam reflected off of the respective receiving spots (hereafter also referred to as reflected detection beam), and generates the beat signal 93 indicating the detected ultrasonic wave echoes.

The beat signal 93 has a waveform obtained through FM modulation of the carrier wave. Information on the shape and micro vibrations of the surface of the examination target 11 can be obtained through the demodulation of the beat signal 93 by the receiving unit 14 and the position detecting unit 15. The specific configuration and the signal detection principle of the optical probe 13A shall be described in detail later.

Furthermore, the signal processing unit 16 includes a signal storage unit 16a, a position storage unit 16b, an arithmetic processing unit 16c, and an image memory 16d.

The signal storage unit 16a stores the detection signal 94 generated by the receiving unit 14. The position storage unit 16b stores the relative position information 95 generated by the position detecting unit 15.

The arithmetic processing unit 16c generates image data 99 by performing a beam forming processing based on the detection signal 94 stored in the signal storage unit 16a and the relative position information 95 stored in the position storage unit 16b.

The image memory 16d stores, as the three-dimensional data 96, the image data 99 generated by the arithmetic processing unit 16c.

The outline configuration of the probe unit 82 shall be described below.

Figure 3:
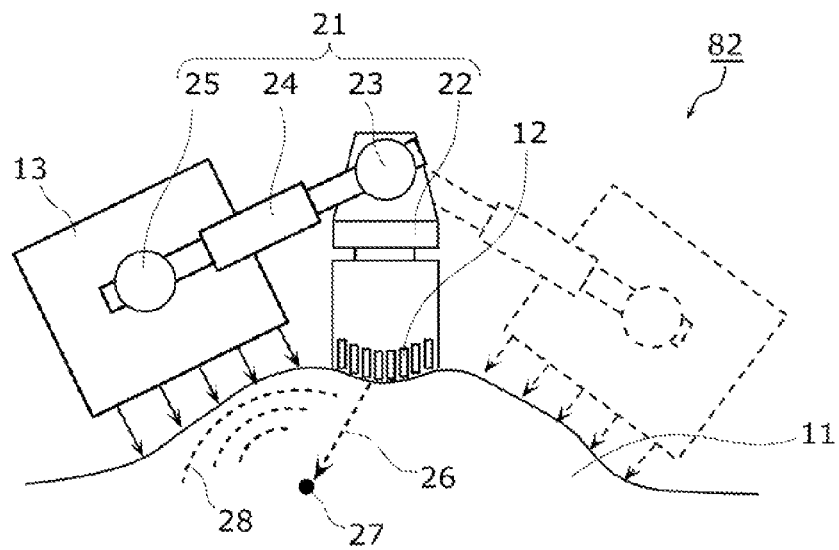
FIG. 3 is a diagram showing the configuration of a probe unit according to Embodiment 1 of the present disclosure.

FIG. 3 is a diagram showing the outline configuration of the probe unit 82. In FIG. 3, the examination target 11 is a breast, and the transmitting probe 12 is placed in the vicinity of the nipple. Furthermore, the transmitting probe 12 transmits the ultrasonic waves 26 to the inside of the examination target 11, in a state where the transmitting probe 12 is in contact with the examination target 11.

The driving unit 21 keeps the relative positional relationship and relative angle between the receiving probe 13 and the transmitting probe 12 fixed, and at the same time, is capable of changing such relative positional relationship and relative angle. The driving unit 21 moves the receiving probe 13 in a state where the transmitting probe 12 is kept fixed. The driving unit 21 includes rotating mechanisms 22 and 23, a telescopic support arm 24, and a rotating mechanism 25.

Specifically, the receiving probe 13 is held with respect to the transmitting probe 12, via the rotating mechanisms 22, 23, the as support arm 24, and the rotating mechanism 25. Here, the rotating mechanism 22 is configured so as to allow the receiving probe 13 to revolve with the transmitting probe 12 as the center. Furthermore, the rotating mechanism 23 has an axis of rotation that is orthogonal with respect to the axis of rotation of the rotating mechanism 22. In addition, changing the length of the support arm 24 allows the distance between the receiving probe 13 (optical probe 13A) and the transmitting probe 12 to be adjusted. As such, with the combination of the rotating mechanism 22, the rotating mechanism 23, and the support arm 24, the receiving probe 13 can move three-dimensionally with respect to the transmitting probe 12. Furthermore, the rotating mechanism 25 allows the angle between the surface of the examination target 11 and the receiving probe 13 (the angle formed by the support arm 24 and the receiving probe 13) to be adjusted. It should be noted that although, here, the transmitting probe 12 is placed in the vicinity of the nipple, the transmitting probe 12 may be placed elsewhere on the breast other than the nipple.

Here, the rotating mechanisms 22, 23, and 25, and the support arm 24 include a servo motor, a stepping motor, or a solenoid, and the like, that allows positioning control. Furthermore, the position detecting unit 15 detects the relative positional relationship (second relative positional relationship) and relative angle between the transmitting probe 12 and the receiving probe 13, from the positioning data 92 which is outputted from the driving unit 21 and indicates the relative positional relationship and relative angle between the receiving probe 13 and the transmitting probe 12.

Here, the position of the transmitting probe 12 is the transmitting position of the ultrasonic waves, and refers to one point on the transmitting probe 12 (or on the examination target 11). Specifically, such transmitting position can be defined by the intersection between the straight line extending in the traveling direction of the wavefronts of the ultrasonic waves 26 and passing the convergence point of the ultrasonic waves 26 (here, a reflective tissue 27) and the transmitting probe 12.

Furthermore, the position of the receiving probe 13 is the emitting position of each of the detection beams of the optical probe 13A. Furthermore, the receiving position of the ultrasonic waves refers to the position at which the receiving spots are formed on the surface of the examination target 11.

Here, the distance between the transmitting position of the ultrasonic waves and the emitting position of each of the detection beams of the optical probe 13A can be calculated using information on the angle of rotation of the rotating mechanisms 22, 23, and 25 and the length of the support arm 24. Therefore, when the relative positional relationship between the emitting position and the receiving spot of each of the detection beams of the optical probe 13A is known, the relative positional relationship between the transmitting position of the ultrasonic waves and the receiving spots can be calculated.

It should be noted that the emitting positions of the detection beams are arranged at approximately equal intervals on the surface of the optical probe 13A. Therefore, if the relative position of the center point of the optical probe 13A with respect to the transmitting position of the ultrasonic waves can be calculated, the position of an emitting point of a detection beam present outside the center point of the optical probe 13A can be calculated using such relative position. It should be noted that the method of detecting the relative positional relationship between the emitting position and the receiving spot of each of the detection beams of the optical probe 13A shall be described in detail later.

Figure 4:
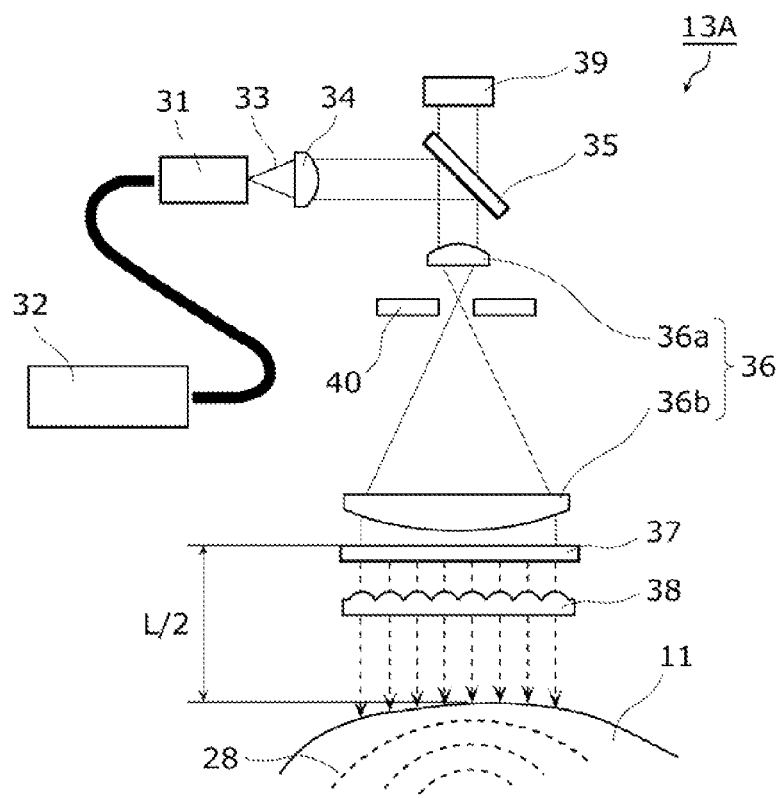
FIG. 4 is a diagram showing the configuration of an optical probe according to Embodiment 1 of the present disclosure.

FIG. 4 shows a diagram of the outline configuration of the optical probe 13A. As shown in FIG. 4, the optical probe 13A includes a semiconductor laser 31, a current modulator 32, a collimating lens 34, a polarized-light beam splitter 35, a beam expander 36, the polarized-light reflecting plate 37, a microlens array 38, and a light-receiving element 39.

The semiconductor laser 31 and the current modulator 32 are the first light source which emits a laser beam 33. The semiconductor laser 31 has an operating interval in which injection current and emission wavelength are locally linearly-varying. The current modulator 32 modulates the current to be supplied to the semiconductor laser 31. The collimating lens 34 collimates the laser beam 33 emitted by the semiconductor laser 31.

The polarized-light beam splitter 35 is a splitting element which splits the laser beam 33 into the detection beam with which the examination target 11 is irradiated and the reference beam which advances in the opposite direction as the detection beam. The polarized-light beam splitter 35 allows the P polarized light component to pass and reflects the S polarized light component.

The beam expander 36 includes lenses 36a and 36b. The polarized-light reflecting plate 37 is configured of, for example, a wire grid polarized-light plate. The polarized-light reflecting plate 37 allows a polarized light component in the transmission axis direction to pass and reflects a polarized light component that is orthogonal to the transmission detection. The microlens array 38 forms plural receiving spots by condensing, on the examination target 11, the light that has passed though the polarized-light reflecting plate 37. The beam expander 36, the lenses 36a and 36b, the polarized-light reflecting plate 37, and the microlens array 38 are the irradiating optics system which divides the detection beam into plural beams and irradiates the examination target 11 with the beams to form plural receiving spots on the examination target 11.

Each of light-receiving areas of the light-receiving element 39 receives the interfering light of the reference beam and the reflected detection beam which is the detection beam that is reflected off of a corresponding one of the receiving spots, and generates a beat signal 93 that is in accordance with the received interference light. Furthermore, the light-receiving areas of the light-receiving element 39 correspond 1-to-1 with the receiving spots on the examination target 11.

Here, the current modulator 32 superimposes a sawtooth-like current on the injection current. With this, the semiconductor laser 31 emits a laser beam 33 that has been sawtooth frequency-modulated. It should be noted that, the transmitting probe 12 may include, in place of the current modulator 32, a modulator that performs sawtooth modulation of the optical frequency of the laser beam 33. Even in such a case, it is also possible to generate the sawtooth frequency-modulated laser beam 33.

Furthermore, the polarized-light reflecting plate 37 is configured such that its transmission axis is tilted approximately 45 degrees with respect to the S polarized light of the polarized-light beam splitter 35. Therefore, part of the light incident on the polarized-light reflecting plate 37 is reflected and part passes through.

It should be noted that the microlens array 38 is configured so as to form plural receiving spots. The receiving spots may be arranged in one column in a predetermined direction, or may be arranged in a two-dimensional matrix.

Furthermore, when a detection beam reflected off of a receiving spot on the examination target 11 enters a lens different from that in the outward route when re-entering the microlens array 38, the detection beam does not enter the corresponding light-receiving area on the light-receiving element 39. Since such light becomes a stray light, the light is blocked by an aperture 40.

Figure 5:
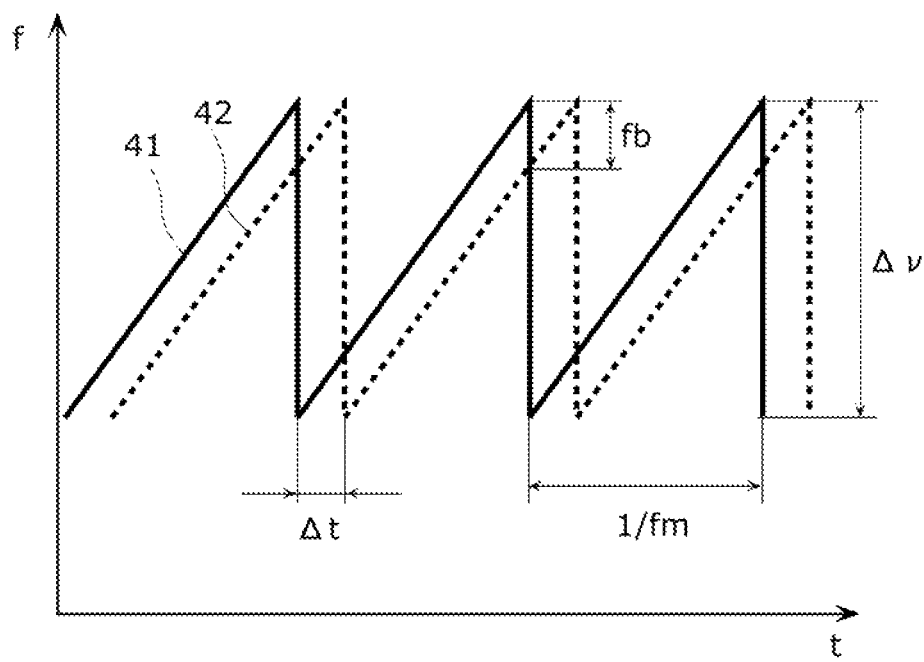
FIG. 5 is a graph showing signal wavelengths of a reference beam an a detection beam according to Embodiment 1 of the present disclosure.

FIG. 5 is a graph showing the signal waveforms of the reference beam and the reflected detection beam that are detected by the light-receiving element 39 of the optical probe 13A. The vertical axis of the graph denotes the optical frequency (f), and the horizontal axis denotes time (t). It should be noted that a reference beam means a light that is reflected off of the polarized-light reflecting plate 37, and reflected detection beam means a detection beam that has passed through the polarized-light reflecting plate 37 and is reflected back from the surface of the examination target 11.

As shown in FIG. 5, a signal waveform 41 of the reference beam and a signal waveform 42 of the reflected beam are waveforms having a deviation of a time Δt. This is because, after the reference beam and the detection beam are split by the polarized-light reflecting plate 37, there is an optical path difference in the paths that each of the light beams pass through until reaching the light-receiving element 39. Here, when the distance between the polarized-light reflecting plate 37 and the surface of the examination target 11 is assumed to be L/2 and light speed is assumed to be c, the optical path difference is L, and thus the signal waveforms have a deviation of Δt=L/c. At this time, since a slight difference is generated between the optical frequencies of the reference beam and the reflected detection beam received by the light-receiving element 39, a beat signal 93 of such differential frequency (hereafter referred to as beat frequency) fb=Δv·fm·Δt is detected by the light-receiving element 39.

For example, when the cyclic frequency fm of the sawtooth wave of the laser beam 33 is fm=10 MHz, the fluctuation range Δv of the optical frequency is Δv=15 GHz, and the optical path difference L between the reference beam and the detection beam is L=40 mm, the beat frequency fb is 20 MHz. At this time, when the length of L shifts by 0.01 mm, the beat frequency shifts by 5 kHz. Therefore, by accurately measuring the beat frequency, the distance between the polarized-light reflecting plate 37 and the examination target 11 can be measured accurately.

In addition, when the surface of the examination target 11 vibrates due to the propagation of the ultrasonic wave echoes 28, the frequency of the detection beam reflected off of the surface of the examination target 11 shifts slightly due to Doppler shifting. With this, the beat signal 93 detected by the light-receiving element 39 is also affected by the Doppler shift in the same manner. As such, the beat signal 93 detected by the light-receiving element 39 becomes an FM signal having the beat frequency as a central frequency. By demodulating this FM signal, it is possible to detect the vibrations caused by the ultrasonic wave echoes 28 that have been reflected inside the examination target 11.

For example, when the variable amplitude of the surface of the examination target 11 due to the ultrasonic wave echoes 28 is assumed to be 0.5 nm, and the frequency of the ultrasonic wave echoes 28 is assumed to be 5 MHz, the fluctuation velocity v of the surface of the examination target 11 is at most 0.0157 m/s. At this time, assuming light source wavelength λ=683 nm, the Doppler shift frequency fb will be fb=4πv/λ=289 kHz. Therefore, when the beat frequency is 20 MHz, the frequency of the beat signal 93 detected by the light-receiving element 39 is FM-modulated between 19.71 to 20.29 MHz.

Figure 6A:
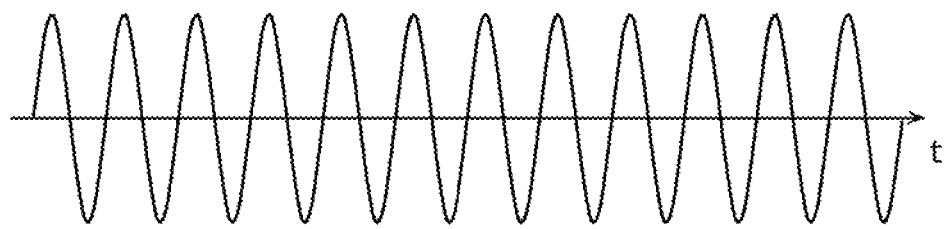
FIG. 6A is a diagram showing an output wavelength of a light-receiving element of the optical probe according to Embodiment 1 of the present disclosure.
Figure 6B:
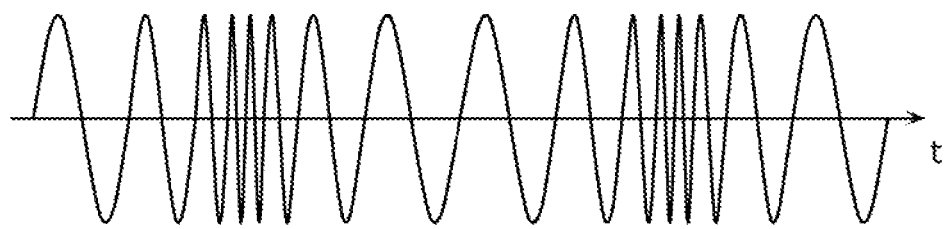
FIG. 6B is a diagram showing an output wavelength of the light-receiving element of the optical probe according to Embodiment 1 of the present disclosure.

FIG. 6A and FIG. 6B are diagrams showing the output waveform (beat signal 93) of the light-receiving element 39 of the optical probe 13A. FIG. 6A shows the output waveform when there is no Doppler shift, and FIG. 6B shows the output waveform when there is a Doppler shift. When there is no vibration at the surface of the examination target 11 (that is, when there is no propagation of the ultrasonic wave echoes 28), a carrier wave of a beat frequency that is in accordance with the optical path difference L between the reference beam and the detection beam, as shown in FIG. 6A, is detected. The position detecting unit 15 can calculate the optical path difference L using the beat frequency. In addition, the position detecting unit 15 can calculate the relative positional relationship (first relative positional relationship) between the receiving spot and the receiving probe 13.

Furthermore, when the ultrasonic wave echoes 28 reach the surface of the examination target 11, the surface of the examination target 11 vibrates. When the surface of the examination target 11 vibrates, the carrier waves are FM-demodulated as shown in FIG. 6B. By FM-demodulating such signal, the receiving unit 14 can generate a detection signal 94 indicating the microscopic displacement of the surface of the examination target 11 due to the ultrasonic wave echoes 28.

It should be noted that the detection beam is divided into plural beams by the microlens array 38, and the light-receiving element 39 is also split into plural light-receiving areas according to the branch areas of the beams. Furthermore, plural light-receiving elements may be separately provided. By calculating respective beat frequencies from the signals obtained in the light-receiving areas, the distance between the optical probe 13A and the examination target 11 can be more accurately detected even when the surface of the examination target 11 is curved as in FIG. 3.

As described above, by configuring the transmitting probe 12 and the optical probe 13A, which is a receiving probe, as separate bodies such that the optical probe 13A does not come into contact with the body surface, it becomes possible to reduce the amount of deformation that occurs in the examination target 11 during examination in the case where the examination start time is assumed as the criterion.

It should be noted that although a configuration is adopted in which the transmitting probe 12 transmits ultrasonic waves three-dimensionally from one transmitting point, ultrasonic waves may be transmitted over a wide area by using plural ultrasound probes.

However, having fewer parts of the probes coming into contact with the examination target allows the amount of deformation of the examination target to be kept minimal.

Furthermore, the configuration of pressing down only on the nipple which is facing upward has the advantage in that it is easy to reproduce the state of deformation before surgery and verifying the position for surgery is easy.

Meanwhile, in performing beam forming using the detection signal 94, assuming that a hypothetical sound source in phase rectifying addition is the focus point, the distance between the transmitting point at which the ultrasonic waves 26 are transmitted and the focus point, and the distance from the focus point to the respective receiving spots need to be known. Since the transmitting positions and the receiving positions are conventionally arranged at equal intervals on the same plane, it is easy to calculate the distances between them. On the other hand, in the present configuration, since the detection signal 94 is detected by forming receiving spots on the curved surface having an uncertain shape, it is necessary to measure the three-dimensional position of each of the receiving spots with respect to the transmitting position of the ultrasonic waves 26.

Figure 7A:
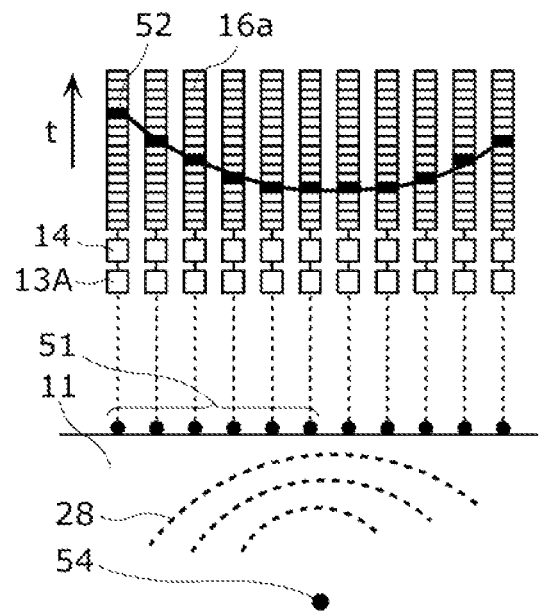
FIG. 7A is diagram showing delay time when receiving spots are on a flat surface.
Figure 7B:
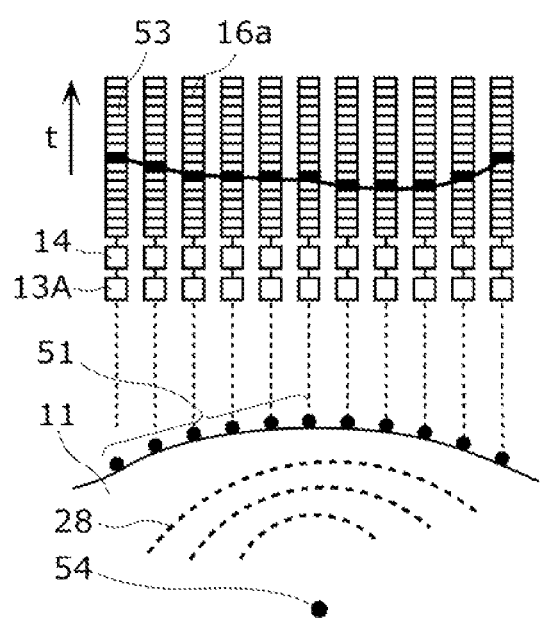
FIG. 7B is diagram showing delay time when receiving spots are on a curved surface.

FIG. 7A and FIG. 7B are diagrams showing the delay time when in-phase signals are detected. FIG. 7A shows the delay time when receiving spots are on a flat surface. FIG. 7B shows the delay time when receiving spots are on a curved surface.

As shown in FIG. 7A, when the respective receiving spots 51 are formed at equal intervals on a flat surface, it is possible to calculate the distance from the focus point 54 to each of the receiving spots 51. Therefore, the signal processing unit 16 can perform beam forming by calculating the delay time 52 based on this distance.

On the other hand, as shown in FIG. 7B, when the receiving spots 51 are formed on a curved surface having an uncertain shape, the distance from the focus point 54 to each of the receiving spots 51 is uncertain. Therefore, the signal processing unit 16 cannot calculate the delay time 53 and is thus unable to perform beam forming. Therefore, it becomes necessary to calculate the three-dimensional position of each receiving spot.

In this embodiment, the position detecting unit 15 calculates the relative positional relationship between the transmitting positions of the ultrasonic waves 26 and the receiving spots, using the relative positional relationship between the transmitting probe 12 and the optical probe 13A, and the distance L/2 between the optical probe 13A and the receiving spots on the examination target 11.

Specifically, the position detecting unit 15 detects the relative positional relationship (second relative positional relationship) and relative angle between the transmitting probe 12 and the optical probe 13A, from the positioning data 92 of the driving unit 21. Furthermore, as described above, the position detecting unit 15 calculates the first relative positional relationship between each of the receiving spots and the optical probe 13A, from the frequency of the beat signal 93. In addition, the position detecting unit 15 calculates a third relative positional relationship between the transmitting probe 12 and the respective receiving spots, from the first relative positional relationship and the second relative positional relationship, and stores, in the position storage unit 16b, the relative position information 95 indicating the calculated third relative positional relationship. Then, the arithmetic processing unit. 16c computes the time it takes for the ultrasonic wave echoes 28 to reach the receiving spots based on the third relative positional relationship, and generates image data 99 by performing phase rectifying addition on the detection signal 94 using such time.

It should be noted that, in order to calculate the relative position of each receiving spot with respect to the transmitting position of the ultrasonic wave, it is sufficient to adopt a configuration that allows the measurement of the relative position of each receiving spot with respect to the optical probe 13A. This measurement can be implemented, for example, by using a separate sensor for three-dimensional measurement, such as a stereo camera, and the like.

Furthermore, as described earlier, although it is possible to calculate the distance between the receiving spots and the optical probe 13A, there is a possibility that the relative positional relationship between the optical probe 13A and the respective receiving spots cannot be correctly calculated when the angle formed by the traveling direction of the detection beam emitted from the optical probe 13A and the polarized-light reflecting plate 37 is not perpendicular.

In view of this, in this embodiment, in order to perform this measurement, the respective emission angles of the light beams (hereafter referred to as receiving beams) which are emitted from the optical probe 13A and form the respective receiving spots are measured before hand. In this manner, by measuring the emission angle of each of the receiving beams before hand, the length (optical path difference L) of each of the receiving beams can be calculated from the beat frequency of the beat signal 93 as described using FIG. 4 and FIG. 5, and thus the position detecting unit 15 can calculate the relative positions of the receiving spots 51 from the direction (emission angle) and the length (optical path difference L) of each receiving beam.

Next, the operation of the ultrasound examination apparatus 10 according to Embodiment 1, configured in the aforementioned manner, shall be described using FIG. 2 to FIG. 4, and FIG. 8. FIG. 8 is a flowchart showing the operation of the ultrasound examination apparatus 10.

First, the control unit 20 controls the transmitting unit 19 such that the driving signal 98 is generated at a predetermined timing. The transmitting unit 19 performs delay processing for focusing and deflecting the ultrasonic waves 26, according to the control. Then, the transmitting unit 19 supplies the driving signal 98 that has undergone delaying processing, to each of the transducers of the transmitting probe 12 (S101). The transmitting probe 12 transmits the ultrasonic waves 26 from the respective transducers to form predetermined wavefronts, according to the driving signal 98 transmitted from the transmitting unit 19 (S102). The ultrasonic waves 26 travel in a predetermined direction, in accordance with the wavefronts. The ultrasonic waves 26 transmitted from the transmitting probe 12 are reflected off of the reflective tissue 27 inside the examination target 11 and become the ultrasonic wave echoes 28 which are propagated to the surface of the examination target 11.

Here, the driving unit 21 moves the optical probe 13A before hand to a position suitable for the detection of the ultrasonic wave echoes 28 (S103). For example, the driving unit 21 moves the optical probe 13A so that receiving spots for detecting the ultrasonic wave echoes are formed in a cross-section including the transmitting direction of the ultrasonic waves 26. Subsequently, the optical probe 13A performs the receiving of the ultrasonic wave echoes 28 (S104) and the measuring of the receiving position of the ultrasonic wave echoes 28 (S105).

The signal receiving by the optical probe 13A is performed according to the operation below. First, the current modulator 32 modulates the injection current. With this, the semiconductor laser 31 emits the frequency-modulated laser beam 33. The beam expander 36 expands the laser beam 33. The polarized-light reflecting plate 37 splits the expanded laser beam into the reference beam and the detection beam. The detection beam is emitted so as to form receiving spots on the surface of the examination target 11. The reflected detection beam that is reflected off of each of the receiving spots is received, superimposed with the reference beam, in a corresponding one of the light-receiving areas on the light-receiving element 39.

At this time, the polarization directions of the reference beam and the detection beam bisect each other immediately after the reference beam and the detection beam are reflected off of the polarized-light reflecting plate 37 and the examination target 11, respectively. Furthermore, since the polarization direction of both the reference beam and the detection beam are tilted approximately 45 degrees with respect to the P polarized light of the polarized-light beam splitter 35, the respective P polarized light components of the reference beam and the detection beam pass through the polarized-light beam splitter 35. In this manner, since components of the same polarization direction pass through, the reference beam and the detection beam interfering with each other are received by the light-receiving element 39.

The beat signal 93 detected in this manner is a signal that is FM-modulated with a beat frequency that is in accordance with the optical route difference between the reference beam and the detection beam, as a central frequency. Therefore, the receiving unit 14 generates a detection signal 94 corresponding to the ultrasonic wave echoes 28 by demodulating the FM-demodulation of the beat signal 93.

Furthermore, the position detecting unit 15 calculates the distance between the respective receiving spots and the optical probe 13A, from the beat frequency. It should be noted that, when the emission angle of the receiving beam with respect to the optical probe 13A is not perpendicular, the position detecting unit 15 may calculate the relative positional relationship between the optical probe 13A and the respective receiving spots by adding, to such distance information, the emission angle information of the receiving beam that was measured before hand. Then, the position detecting unit 15 calculates the relative position of each receiving spot with respect to the transmitting position of the ultrasonic waves 26, from the relative position of each receiving spot with respect to the optical probe 13A and the positioning data 92 of the driving unit 21.

It should be noted that the optical probe 13A detects the ultrasonic wave echoes 28 without contact with the examination target. Furthermore, in the case of this embodiment, image information of an extensive area can be obtained by moving the optical probe 13A without moving the transmitting probe 12. As such, problems such as the deterioration of signals to be detected due to the level of indentation pressure or the angle of a conventional probe do not occur. Furthermore, compared with the conventional ultrasound examination apparatus, it is possible to reduce the change in shape between the state of deformation of the examination target 11 at the start of examination and the subsequent states of deformation of the examination target 11. As such, since the effect of the deformation of the examination target 11 included in each diagnostic image comes close to becoming constant, there is little need to individually perform compensation of the deformation of the examination target 11 for the obtained diagnostic images.

Furthermore, since the positional relationship with respect to the optical probe 13A can be calculated for each receiving spot, the phase rectifying addition of the received signal can be performed even when the surface of the examination target 11 is curved. With this, examination can be performed using a larger aperture, and thus high resolution can be obtained.

Furthermore, since the optical probe 13A detects the ultrasonic wave echoes 28 from the vibrations at the surface of the examination target 11, when the skin surface is tilted with respect to the receiving beam, amplitude of oscillation caused by the ultrasonic wave echoes 28 become visually small, and thus contrast deteriorates. In response to this, in this embodiment, the control unit 20 calculates the tilt angle at each receiving spot by estimating the shape of the surface of the examination target 11 from the three-dimensional position (first relative information) of each receiving spot that is measured. Then, the control unit 20 can prevent the deterioration of contrast by adjusting the amplitude of the displacement (oscillation amplitude) detected at the receiving spot, according to such tilt angle. Specifically, the control unit 20 increases the oscillation amplitude when the angle of tilt is greater than a predetermined threshold. Furthermore, the control unit 20 increases the oscillation amplitude as the angle of tilt is larger. For example, the control unit 20 increases the oscillation amplitude by increasing the gain of the receiving unit 14 with respect to the beat signal 93. Alternatively, the control unit 20 increases the oscillation amplitude by increasing the intensity of the detection beam emitted by the transmitting probe 12.

It should be noted that although the amount of reflected light decreases when the skin surface is tilted with respect to the optical probe 13A, this does not pose a problem since the oscillation amplitude is detected from the frequency of the FM-modulated beat signal 93.

Description is once again carried out with reference to FIG. 8. The receiving unit 14 demodulates the beat signal 93 generated by the optical probe 13A, and further performs amplification and digital conversion to generate the detection signal 94 (S106). The detection signal 94 is stored in the signal storage unit 16a of the signal processing unit 16. Furthermore, the relative position information 95 (third relative positional relationship) of each receiving spot with respect to the transmitting position of the ultrasonic waves 26, which is detected by the position detecting unit, is stored in the position storage unit 16b.

Next, the arithmetic processing unit 16c generates image data 99 by performing beam forming processing on the region following the transmission path (hereafter referred to as sound ray), based on the detection signal 94 stored in the signal storage unit 16a and the relative position information 95 stored in the position storage unit 16b (S107). Then, the image data 99 obtained from such processing is stored in the image memory 16d.

The above-described operation takes place while the sound ray of the ultrasonic waves 26 transmitted from the transmitting probe 12 moves inside the examination target. Specifically, when the scanning of all the regions to be examined has not been completed (No in S108), the processes in steps S103 to S107 are performed. Then, when the scanning of all the regions to be examined is completed (Yes in S108), the image data 99 of all the regions to be examined is arithmetic-processed and stored in the image memory 16d.

It should be noted that, at this time, the transmitting probe 12 three-dimensionally transmits the ultrasonic waves 26, while being in a fixed position. Furthermore, the optical probe 13A performs non-contact signal detection while moving to a position that facilitates receiving of the ultrasonic wave echoes 28 in accordance with the direction of the sound ray of the ultrasonic waves 26. In this manner, when the transmitting probe 12 which transmits the ultrasonic waves 26 and the optical probe 13A which receives the ultrasonic wave echoes 28 are configured as separate bodies, the propagation path of the ultrasonic wave echoes 28 can be shortened particularly in the case where the scanning angle is large. Therefore, it is possible to perform signal detection in which there is a large number of apertures for receiving and there is also little attenuation. This makes it possible to perform scanning with high resolution and contrast, over a large area.

Next, the image processing unit 17 generates a three-dimensional image 97 by performing three-dimensional image rendering of the three-dimensional data 96 which is the plural items of image data 99 stored in the image memory 16d (S109). Subsequently, the three-dimensional image 97 obtained through such processing is displayed on the image displaying unit 18.

As described thus far, when the deformation of the examination target at the start of examination is assumed as the criterion, the ultrasound examination apparatus 10 according to this embodiment can reduce the deformation of the examination target 11 after the start of the examination compared to conventional ultrasound examination apparatuses. Accordingly, the ultrasound examination apparatus 10 can easily obtain, as a three-dimensional image, a more accurate total image of the breast. Therefore, since it is possible to obtain a three-dimensional total image which has high reproducibility and allows a doctor to display and interpret a tomographic image of an arbitrary cross-section, efficient diagnosis can be carried out.

In addition, the ultrasound examination apparatus 10 according to this embodiment can realize an ultrasound examination apparatus which allows examination without deformation of the breast, and is thus capable of providing a breast cancer examining apparatus suited to automatic measurement. Accordingly, since it is possible to obtain an examination result that is not dependent on the examiner, breast cancer examination can be performed with an all-female staff, for example. With this, more women will more readily undergo breast cancer screening.

Furthermore, unlike with the conventional direct contact method, with the ultrasound examination apparatus 10 according to this embodiment, there is little image deterioration due to the indentation pressure and angle of the probe. As such, there is little need to perform scanning while checking the ultrasound images, and thus the ultrasound examination apparatus 10 is further suitable for to an automated examination apparatus. In addition, since the optical probe 13A can be moved with respect to the transmitting probe 12, excellent ultrasound images can be obtained even when the scanning angle of the ultrasonic waves transmitted is large. This makes it possible to perform scanning with high resolution and contrast, over a large area.

It should be noted that although description of configurations in this embodiment is carried out assuming an automated apparatus, application to a form in which examination is performed by a technician who manually moves the optical probe 13A is also possible.

Figure 9A:
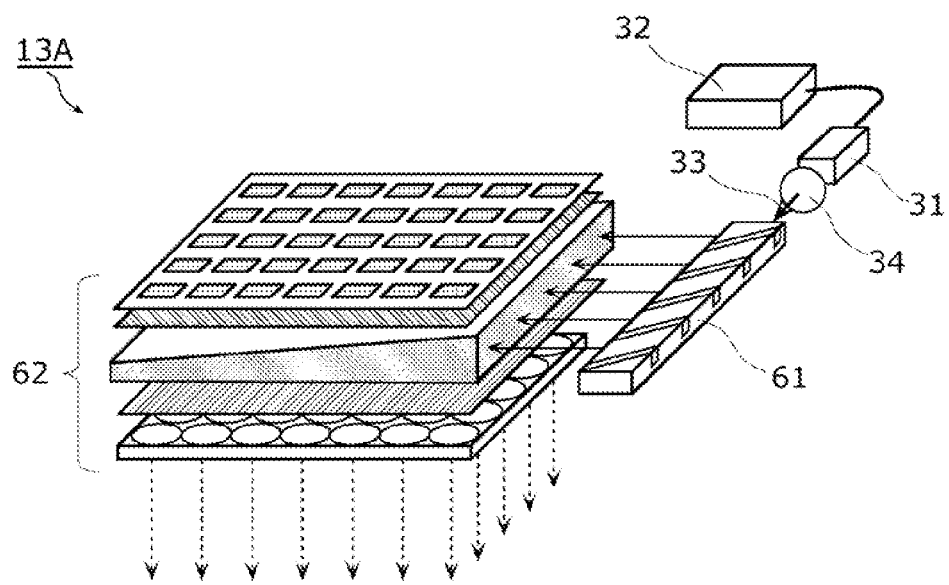
FIG. 9A is a perspective view of an optical probe according to Modification 1 of Embodiment 1 of the present disclosure.
Figure 9B:
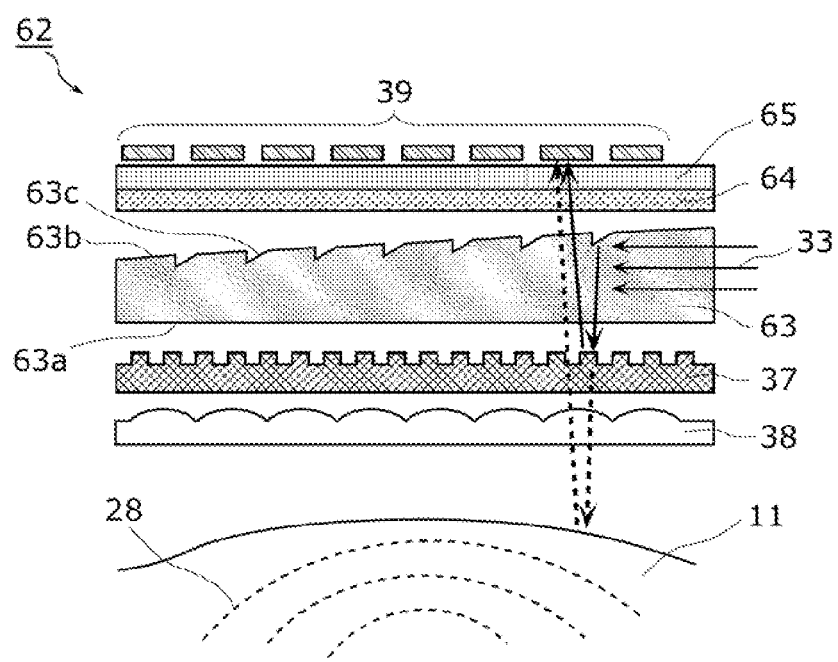
FIG. 9B is a cross-sectional view of the optical probe according to Modification 1 of Embodiment 1 of the present disclosure.

FIG. 9A and FIG. 9B are diagrams showing the configuration of the optical probe 13A that has been miniaturized under the assumption of manual operation. FIG. 9A is a perspective view of the optical probe 13A in such a case. FIG. 9B is a cross-sectional view of main parts of the optical probe 13A. It should be noted that, in FIG. 9A and FIG. 9B, constituent elements that are the same as those in FIG. 4 are assigned the same reference signs as in FIG. 4 and their description shall not be repeated.

As shown in FIG. 9, the optical probe 13A includes the semiconductor laser 31, the current modulator 32, the collimating lens 34, a light-guiding bar 61 which converts the laser beam 33 into linear parallel light beams, and a planar detecting unit 62.

Here, plural deflecting trenches having a tilted face which is tilted approximately 45 degrees with respect to a side face at which the light is emitted are formed in the light-guiding bar 61. The light-guiding bar 61 deflects light incident on the light-guiding bar 61, 90 degrees by total reflection.

Furthermore, the planar detecting unit 62 is configured, for example, in the structure shown in FIG. 9B. The planar detecting unit 62 includes a light-guiding plate 63, the polarized-light reflecting plate 37, the microlens array 38, a polarized-light plate 64, a view angle control sheet 65, and the light-receiving element 39.

The laser beam 33 emitted from the light-guiding bar 61 enters the light-guiding plate 63 from a side face. The light-guiding plate 63 emits the laser beam 33 incident thereon, from one main face 63*a*.

The polarized-light reflecting plate 37 is disposed adjacent to the main face 63*a* of the light-guiding unit 63. The polarized-light plate 64 is disposed on a side of the light-guiding unit 63 that is opposite the polarized-light reflecting plate 37.

Out of the light that has passed through the polarized-light plate 64, the view angle control sheet 65 allows only light entering approximately perpendicularly. The light-receiving element 39 has plural light-receiving areas which correspond respectively to the receiving spots on the examination target 11.

It should be noted that plural deflecting faces 63*c*, each configured of a tilted face that is tilted approximately 45 degrees with respect to the main face 63*a*, are formed in an opposite side 63*b* of the light-guiding plate 63. With this, the light-guiding plate 63 can deflect light entering approximately parallel to the main face 63*a*, towards the main face 63*a* by total reflection, and emit light approximately perpendicularly from the main face 63*a*.

Furthermore, the transmission axis of the polarized-light plate 64 forms a 45 degree angle with the transmission axis of the polarized-light reflecting plate 37. Furthermore, the view angle control sheet 65 is provided to prevent, for each of the light-receiving areas of the light-receiving element 39, stray light from a non-corresponding receiving spot from mixing in.

In the optical probe 13A configured in the above-described manner, the frequency-modulated laser beam 33 is collimated by the collimating lens 34, converted into linear parallel light beams by the light-guiding bar 61, and enters the planar detecting unit 62. The laser beams 33 incident on the light-guiding plate 63 of the planar detection unit 62 are deflected by the deflecting faces 63*c*, emitted approximately perpendicularly from the main face 63*a* of the light-guiding plate 63, and split into the reference beams and the detection beams by the polarized-light reflecting plate 37. The detection beams form plural receiving spots on the surface of the examination target 11 via the microlens array 38. The detection beam reflected off of each receiving spot and the reference beam reflected by the polarized-light reflecting plate 37 pass through the light-guiding plate 63 and enter the polarized-light plate 64. Here, although the polarization directions of the reference beam and the detection beam are orthogonal to each other, both polarization directions turn approximately 45 degrees with respect to the transmission axis of the polarized-light plate 64. Therefore, respective lights of the same polarized light component of the reference beam and the detection beam pass through the polarized-light plate 64, and only the lights which pass approximately perpendicularly pass through the view angle control sheet 65 and interfere in the light-receiving element 39. Then, the interfering lights are detected in the respective light-receiving areas of the light-receiving element 39.

Even with such a configuration, the distance between the examination target 11 and the optical probe 13A can be calculated from the beat frequency of the detected beat signal 93, and by demodulating the FM modulation, the vibrations at each of the receiving spots can be detected.

Therefore, the configuration described above provides an optical probe that is small and thin, but capable of reducing the deformation of the examination target 11 occurring during examination. With this, it is possible to realize an ultrasound examination apparatus having high reproducibility and high resolution.

Furthermore, although, in this embodiment, the detection of the relative positional relationship and relative angle between the transmitting probe 12 and the receiving probe 13 is performed using the positioning information of the driving unit 21, using an infrared ray sensor or gyro detection, and so on, would allow a configuration in which the transmitting probe 12 and the receiving probe 13 are detached.

Figure 10:
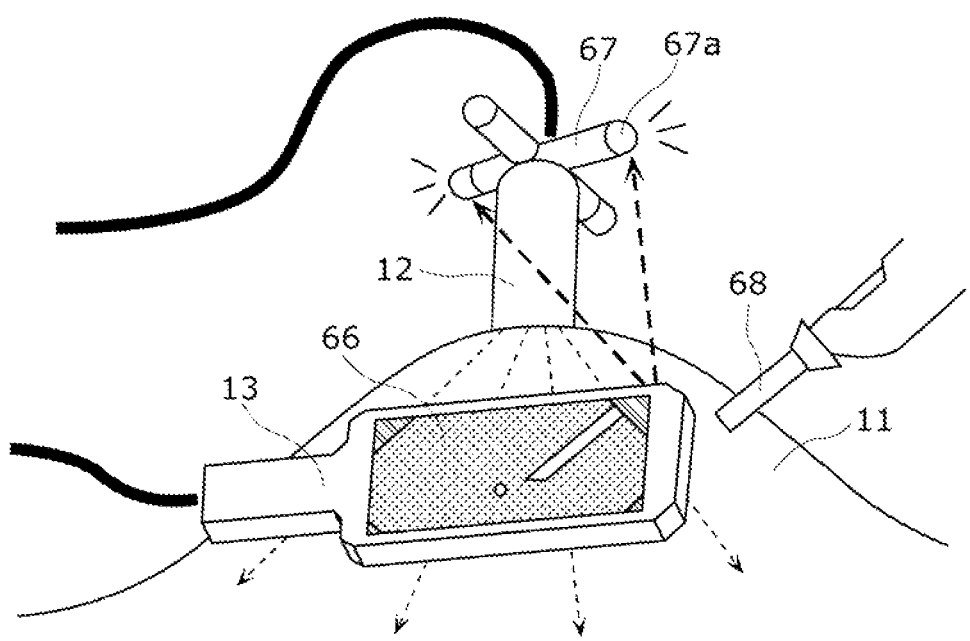
FIG. 10 is a diagram showing an ultrasound examination apparatus according to Modification 2 of Embodiment 1 of the present disclosure.

FIG. 10 is a diagram showing a specific example of a detached-probe configuration. Furthermore, FIG. 11 is a block diagram of the ultrasound examination apparatus 10 in such a case.

As shown in FIG. 10, the transmitting probe 12 further includes two sensor bars 67 arranged so as to be orthogonal to each other. Each of the sensor bars 67 includes two light sources 67*a* (second light sources) which are disposed one on each end of the sensor bar 67. The light source 67*a* is, for example, an infrared LED.

Figure 11:
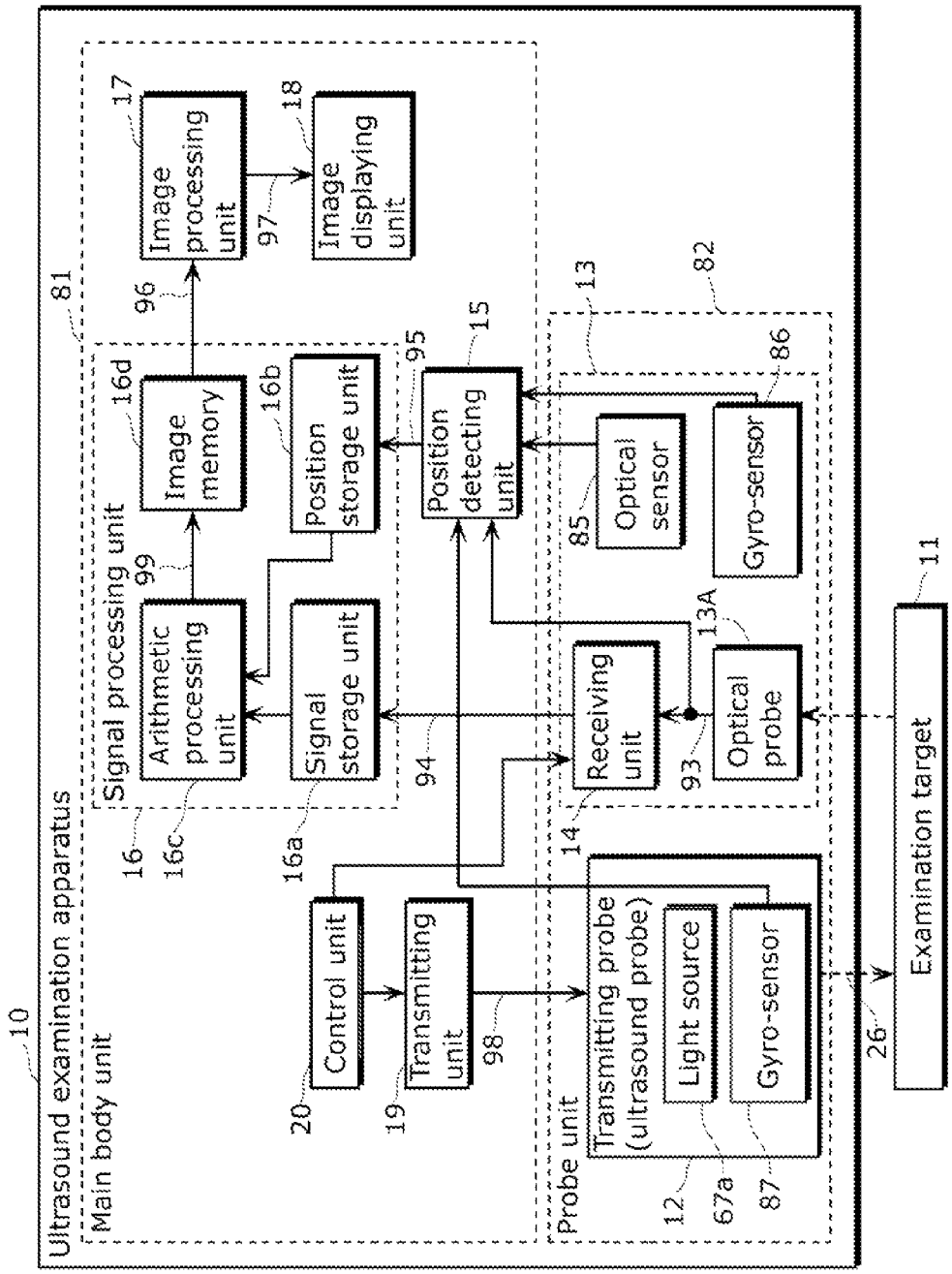
FIG. 11 is a block diagram of the ultrasound examination apparatus according to Modification 2 of Embodiment 1 of the present disclosure.

In addition, as shown in FIG. 11, the transmitting probe 12 includes a gyro-sensor 87 (first gyro-sensor). Furthermore, the receiving probe 13 has the thin configuration described using FIG. 9, and includes a display panel 66 that displays a tomographic image, an optical sensor 85, and a gyro-sensor 86 (second gyro-sensor).

The gyro-sensor 87 detects the orientation of the transmitting probe 12. The gyro-sensor 86 detects the orientation of the receiving probe 13. Then, the position detecting unit 15 detects the relative angle between the transmitting probe 12 and the receiving probe 13 by comparing the orientation of the transmitting probe 12 and the orientation of the receiving probe 13 which are detected by the gyro-sensors.

The optical sensor 85 detects the lights from the light sources 67a, using images. The optical sensor 85 is, for example, a CMOS sensor that constantly takes images of the infrared light produced at the tips of the sensor bars 67. The position detecting unit 15 calculates the positional relationship of the light sources 67a as seen from the optical sensor 85, from the positions of the luminous spots and the spaces therebetween indicated in the images taken by the optical sensor 85, and detects the relative positional relationship between the transmitting probe 12 and the receiving probe 13 from the calculated positional relationship.

It should be noted that although the transmitting probe 12 includes the light sources 67a, and the receiving probe 13 includes the optical sensor 85 here, the transmitting probe 12 may include the optical sensor 85 and the receiving probe 13 may include the light sources 67a.

By adopting such a configuration, the relative positional relationship and the relative angle between the transmitting probe 12 and the receiving probe 13 can be detected even when the transmitting probe 12 and the receiving probe 13 are completely detached, and thus examination can be carried out while a technician freely moves the receiving probe 13 by hand.

Furthermore, at this time, by operating the transmitting probe 12 according to the position of the receiving probe 13 so that the ultrasonic waves 26 transmitted from the transmitting probe 12 move in a direction that is approximately parallel to the receiving probe 13, the displaying panel 66 displays a tomographic image of the inside of the examination target 11 for a cross-section that is approximately parallel to the display surface of the displaying panel 66. This makes it easier for the technician to intuitively judge the position of a tumor and so on. Furthermore, for example, in an examination such as a mammotome biopsy, it allows easy guidance of a needle 68 to a suspected part of the examination target 11.

It should be noted that although, in the exemplary configuration shown in FIG. 10, the detection of the relative positional relationship and relative angle between the transmitting probe 12 and the receiving probe 13 is performed using a gyro-sensor and an infrared ray sensor, the relative positional relationship and relative angle between the transmitting probe 12 and the receiving probe 13 may be detected using a sensor using radio waves, magnetism, or ultrasound. Furthermore, the relative positional relationship and relative angle between the transmitting probe 12 and the receiving probe 13 may be detected by performing image processing on an image taken by a camera.

It should be noted that although the transmitting probe 12 in this embodiment is described as having a structure in which the transducers are two-dimensionally arranged, the transmitting probe 12 may be a mechanical sector probe which causes transducers arranged one-dimensionally to mechanically oscillate inside the probe.

Furthermore, although laser beam is emitted from the optical probe 13A towards the skin surface in this embodiment, light-protecting agent may be applied to the surface of the skin to protect the skin and increase the reflectance at the surface of the skin. As a light-protecting agent, it is possible to use a light-shielding agent which includes, for example, a powder such as titanium oxide, zinc oxide, kaolin, talc, or mica.

Furthermore, although the ultrasound examination apparatus 10 displays the three-dimensional image 97 in this embodiment, a two-dimensional image (tomographic image) may be displayed without generating a three-dimensional image.

Furthermore, although an example of breast cancer examination is described in this embodiment, the ultrasound examination apparatus 10 can be used for the purpose of examining other parts of the human body. In addition, the ultrasound examination apparatus 10 can be used for purposes of examining living bodies in general, other than a human body.

Embodiment 2

In Embodiment 2 of the present disclosure, a projector including an optical probe shall be described.

Figure 12A:
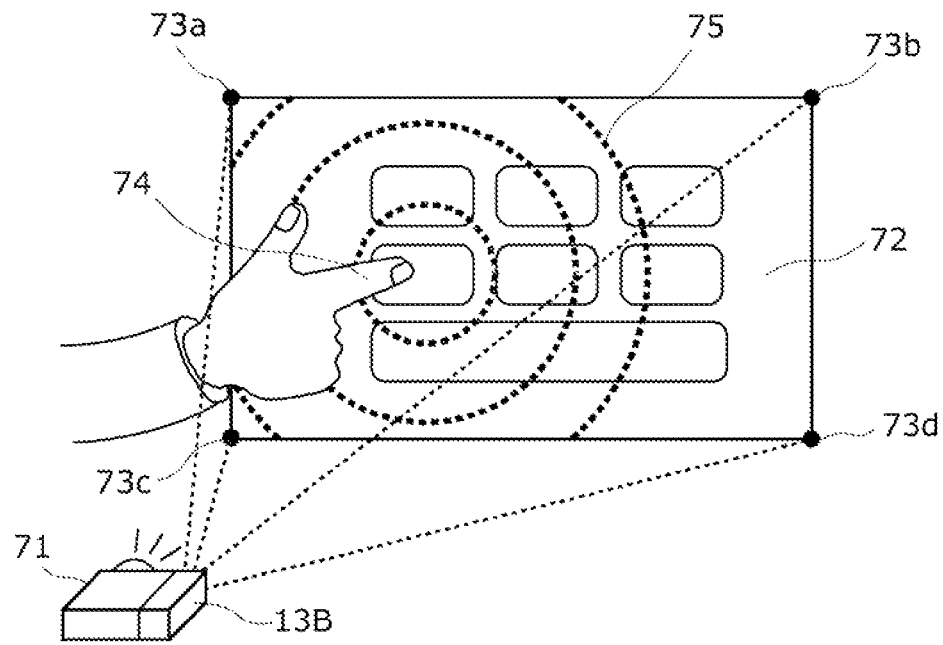
FIG. 12A is diagram showing the configuration of a projector according to Embodiment 2 of the present disclosure.
Figure 12B:
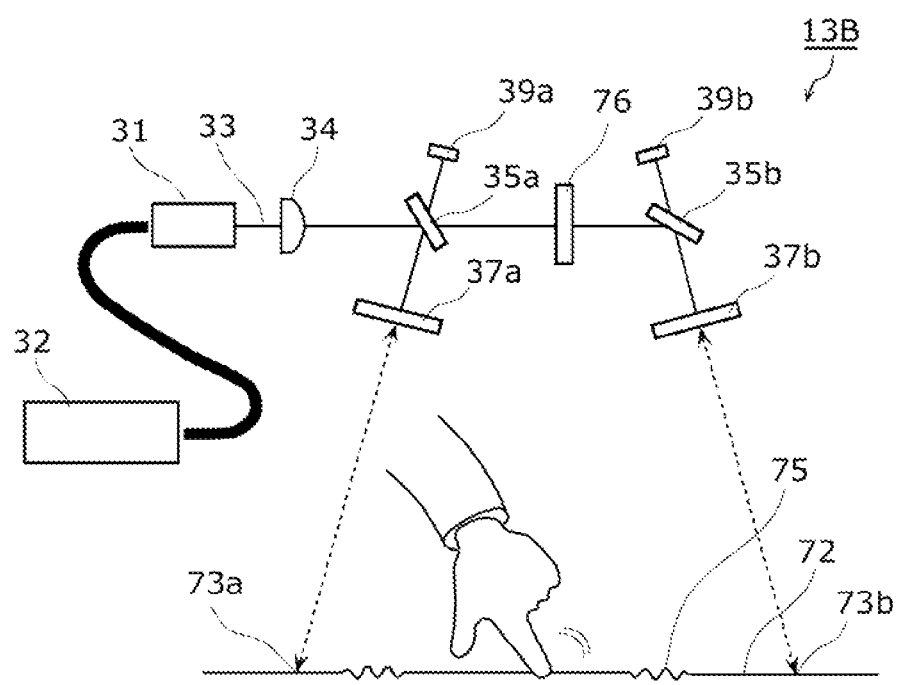
FIG. 12B is diagram for describing the operation of the projector according to Embodiment 2 of the present disclosure.

FIG. 12A is diagram showing the configuration of a projector 71 according to Embodiment 2 of the present disclosure. FIG. 12B is a diagram for describing the operation of an optical probe 13B included in the projector 71. In this embodiment, a configuration obtained by modifying the optical probe 13A described in Embodiment 1 is used for the purpose of touch detection for a projector. It should be noted that among the constituent elements included in the optical probe 13B included in the projector 71, constituent elements that are the same as those in the optical probe 13A described in Embodiment 1 are given the same reference signs as in Embodiment 1, and description thereof shall not be repeated.

As shown in FIG. 12A, the projector 71 projects a video onto a display body 72 such as a screen, a wall, or a table. In addition, the projector 71 includes the optical probe 13B. The optical probe 13B forms, on the display body 72, receiving spots 73a to 73d for detecting vibrations. The receiving spots 73a to 73d detect surface acoustic waves 75 generated when the display body 72 is touched with a finger 74. The projector 71 identifies the position touched by the finger 74 based on a receiving signal detected by the optical probe 13B.

Here, as shown in FIG. 12B, the optical probe 13B includes the semiconductor laser 31, the current modulator 32, the collimating lens 34, polarized-light beam splitters 35a and 35b which reflect the S polarized light component of the laser beam 33, polarized-light reflective plates 37a and 37b each of which has a transmission axis that is tilted approximately 45 degrees with respect to incident polarized light, light-receiving elements 39a and 39b, and a ½ wavelength plate 76 which turns, by 90 degrees, the polarization direction of the light transmitted through the polarized-light beam splitter 35a.

It should be noted that although the optical system forming the receiving spots 73c and 73d have been omitted in order to simplify description in FIG. 12B, the optical system is the same as the optical system forming the receiving spots 73a and 73b shown in FIG. 12B.

In the optical probe 13B configured in the above-described manner, the frequency-modulated laser beam 33 is collimated by the collimating lens 34. In addition, out of the collimated light, the S polarized light component is reflected off of the polarized light beam splitter 35a, and the P polarized light component is allowed to pass through. The P polarized light component that passed through the polarized-light beam splitter 35a is converted to S polarized light by the ½ wavelength plate 76, and is subsequently reflected off of the polarized-light beam splitter 35b. The lights reflected off of the polarized-light beam splitters 35a and 35b are each split into a reference beam and a detection beam by the polarized light reflecting plates 37a and 37b, respectively. The detection beams are emitted onto the display body 72 and form the receiving spots 73a to 73d.

Here, touching a part on the display body 72 using the finger 74 generates surface acoustic waves 75 which have the position touched by the finger 74 as a point of origin. The generated surface acoustic waves 75 propagate on the surface of the display body 72 and eventually reach the receiving spots 73a to 73d. With this, each of the receiving spots vibrate. At this time, the optical frequency of the detection beams shift slightly due to Doppler shift, and the detection beams are reflected.

The detection beams and the reference beams reflected off of the polarized light reflecting plates 37a and 37b enter the polarized-light beam splitters 35a and 35b. P polarized light component of each of these lights pass through the polarized light beam splitter 35a and 35b. Then the interfering light of the detection beam and the reference beam are received on the light-receiving elements 39a and 39b. In addition, the position of each of the receiving spots and the signal corresponding to the surface acoustic waves 75 are detected by the projector 71, from the FM-modulated signal. It should be noted that the detection principle is the same as that in Embodiment 1.

At this time, the position of the point of origin of the surface acoustic waves 75, that is, the position touched by the finger 74 can be calculated from the positions of the respective receiving spots and the time at which the surface acoustic waves 75 are received. With this, the display body 72 can be made to operate like a touch panel.

It should be noted that, by using an infrared light as a light source, it is possible to form many receiving spots on the display body 72. With this, the position that is touched can be accurately detected even when the surface of the display body 72 is curved. Therefore, the projector according to Embodiment 2 is useful because anything that conveys vibrations can be used as a touch panel regardless of shape. Furthermore, since the distance between the receiving spots 73a to 73d on the display body 72 and the projector 71 is known, keystone correction, and the like, can be performed automatically.

As described above, the projector according to Embodiment 2 includes a receiving probe that detects, without contact, the microscopic displacement at plural positions on the surface of the examination target. The receiving probe includes: a light source that emits a laser beam; a splitting element that splits the laser beam into a detection beam and a reference beam; an irradiating optical system that divides the detection beam into plural beams and irradiates an examination target with the plural beams so as to form plural light spots on the surface of the examination target; and plural receiving elements that receive the respective detection beams reflected off of the light spots and receive the reference beam which is superimposed on the respective detection beams. The receiving probe detects, at the light spots, surface acoustic waves generated on the surface of the examination target. The projector detects the generation source of the surface acoustic waves from the positions of the light spots and the time at which vibrations are detected.

It should be noted that the configurations shown in Embodiment 1 and Embodiment 2 are examples, and various modifications can be carried out without departing from the essence of the present inventive concept. Furthermore, it goes without saying that all of the constituent elements may be combined in an arbitrary manner, and each combination produces the unique effects of the present inventive concept.

Furthermore, each of the processing units included in the ultrasound examination apparatus or projector according to the above-described embodiments is typically implemented as an LSI which is an integrated circuit. These processing units may be individually configured as single chips or may be configured so that a part or all of the processing units are included in a single chip.

Furthermore, the method of circuit integration is not limited to LSIs, and implementation through a dedicated circuit or a general-purpose processor is also possible. A Field Programmable Gate Array (FPGA) which allows programming after LSI manufacturing or a reconfigurable processor which allows reconfiguration of the connections and settings of the circuit cells inside the LSI may also be used.

Furthermore, part or all of the functions of the ultrasound examination apparatus or projector according to the embodiments of the present inventive concept may be implemented through the execution of a program by a processor such as a CPU.

In addition, the present inventive concept may be realized as the aforementioned program or a non-transitory computer-readable recording medium on which such program is recorded. Furthermore, it should be obvious that the program can also be distributed via a transmission medium such as the Internet.

Furthermore, at least part of the functions or configuration of the ultrasound examination apparatus, projector, and the modifications thereof, according to the above-described embodiments may be combined.

Furthermore, all the numerical figures used above are given as examples to describe the present inventive concept in specific terms, and thus the present inventive concept is not limited by such illustrative numerical figures. Furthermore, all the materials of the respective constituent elements described above are given as examples to describe the present inventive concept in specific terms, and thus the present inventive concept is not limited by such illustrative materials. Furthermore, the connection relationships among constituent elements are given as examples to describe the present inventive concept in specific terms, and thus the connection relationships for implementing the functions of the present inventive concept are not limited by such examples.

Furthermore, the separation of the function blocks in the block diagrams is merely an example, and plural function blocks may be implemented as a single function block, a single function block may be separated into plural function blocks, or part of functions of a function block may be transferred to another function block. Furthermore, the functions of function blocks having similar functions may be processed, in parallel or by time-sharing, by a single hardware or software.

Furthermore, the sequence in which the above-described steps are executed is given as an example to describe the present inventive concept in specific terms, and thus other sequences are possible. Furthermore, part of the above-described steps may be executed simultaneously (in parallel) with another step.

Although only some exemplary embodiments have been described in detail above, those skilled in the art will readily appreciate that various modifications may be made in these exemplary embodiments without materially departing from the principles and spirit of the inventive concept, the scope of which is defined in the appended Claims and their equivalents.

Industrial Applicability

One or more exemplary embodiments of the present disclosure are applicable to ultrasound examination apparatuses.

One or more exemplary embodiments of the present disclosure are particularly well-suited as breast cancer examining apparatuses.

The invention claimed is:

1. An ultrasound examination apparatus for observing an inside of a body of a living subject, said ultrasound examination apparatus comprising:
   a transmitting probe that transmits ultrasonic waves to an inside of an examination target of the living subject, wherein reflection of the ultrasonic waves from the inside of the examination target causes microscopic displacement on a surface of the examination target;
   a receiving probe including:
      a first light source that emits a laser light;
      a splitting element that splits the laser light into a detection light and a reference light;
      an irradiating optical system that irradiates the examination target with the detection light to form a light spot on the surface of the examination target;
      a light-receiving element that receives an interfering light of the reference light and a reflected detection light which is the detection light reflected off of the light spot, and generates a signal obtained through the reception of the interfering light; and
      a receiving unit configured to generate, using the signal, a detection signal indicating the microscopic displacement on the surface of the examination target at the light spot; and
   a signal processing unit configured to generate image data of the inside of the examination target, based on the detection signal indicating the microscopic displacement during a scanning operation in which said transmitting probe is kept fixed with respect to the examination target and said receiving probe is moved with respect to the examination target,
   and said receiving probe is not in contact with the living subject.

2. The ultrasound examination apparatus according to claim 1,
   wherein the signal is a beat signal, and
   said receiving unit is configured to frequency modulation (FM) demodulate the beat signal to generate the detection signal.

3. The ultrasound examination apparatus according to claim 2, further comprising a position detecting unit configured to calculate a first relative positional relationship between the light spot and said receiving probe, based on a frequency of the beat signal.

4. The ultrasound examination apparatus according to claim 3,
   wherein said position detecting unit is further configured to:
      calculate a second relative positional relationship between said transmitting probe and said receiving probe; and
      calculate a third relative positional relationship between said transmitting probe and the light spot, based on the first relative positional relationship and the second relative positional relationship, and
   said signal processing unit is configured to generate the image data by computing, based on the third relative positional relationship, a time it takes for the reflected ultrasonic waves to reach the light spot, and performing phase rectifying addition on the detection signal using the time.

5. The ultrasound examination apparatus according to claim 4, further comprising a control unit configured to calculate a tilt angle formed, at the light spot, between the surface of the examination target and said receiving probe, and adjust an amplitude of the beat signal according to the tilt angle.

6. The ultrasound examination apparatus according to claim 5, wherein said control unit is configured to calculate the tilt angle by estimating a shape of the surface of the examination target using the first relative positional relationship.

7. The ultrasound examination apparatus according to claim 4, wherein said first light source emits the laser light having a sawtooth-modulated optical frequency.

8. The ultrasound examination apparatus according to claim 7, wherein said position detecting unit is configured to:
   calculate a difference between an optical path of the detection light and an optical path of the reference light, based on the frequency of the beat signal; and
   calculate the first relative positional relationship based on an emission angle of the detection light and the optical path difference.

9. The ultrasound examination apparatus according to claim 4, further comprising a driving unit configured to changeably fix a relative positional relationship and a relative angle between said receiving probe and said transmitting probe,
   wherein said position detecting unit is configured to calculate the second relative positional relationship based on information on the relative positional relationship between said receiving probe and said transmitting probe, the relative positional relationship being set by said driving unit.

10. The ultrasound examination apparatus according to claim 4,
    wherein one of said transmitting probe and said receiving probe includes a plurality of second light sources,
    the other of said transmitting probe and said receiving probe includes an optical sensor that takes an image of said second light sources, and
    said position detecting unit is configured to calculate the second relative positional relationship, based on a positional relationship between said second light sources in the image taken by said optical sensor.

11. The ultrasound examination apparatus according to claim 4,
    wherein said transmitting probe includes a first gyro-sensor that detects an orientation of said transmitting probe,
    said receiving probe includes a second gyro-sensor that detects an orientation of said receiving probe, and
    said position detecting unit is configured to calculate a relative angle formed between said transmitting probe and said receiving probe, by comparing the orientation of said transmitting probe detected by said first gyro-sensor and the orientation of said receiving probe detected by said second gyro-sensor.

12. The ultrasound examination apparatus according to claim 4,
    wherein said signal processing unit is configured to generate three-dimensional data of the inside of the examination target, as the image data of the inside of the examination target,
    said receiving probe further includes:
       a display; and
       an image processing unit configured to generate, from the three-dimensional data, a tomographic image of the inside of the examination target for a cross-section of the inside of the examination target that is approximately parallel to a display surface of said display, and
    said display displays the tomographic image.

13. The ultrasound examination apparatus according to claim 1, further comprising a driving unit configured to changeably fix a relative positional relationship and a relative angle between said receiving probe and said transmitting probe, wherein said driving unit is configured to perform the scanning operation by keeping said transmitting probe fixed with respect to the examination target and moving said receiving probe with respect to the examination target.

14. The ultrasound examination apparatus according to claim 1, wherein said transmitting probe is configured to be in contact with the examination target.

15. An ultrasound examination method for use in an ultrasound examination apparatus for observing an inside of a body of a living subject, wherein the ultrasound examination apparatus includes:
a transmitting probe that transmits ultrasonic waves to the inside of an examination target of the living subject, wherein reflection of the ultrasonic waves from the inside of the examination target causes microscopic displacement on a surface of the examination target; and
a receiving probe including:
a first light source that emits a laser light;
a splitting element that splits the laser light into a detection light and a reference light;
an irradiating optical system that irradiates the examination target with the detection light to form a light spot on the surface of the examination target;
a light-receiving element that receives an interfering light of the reference light and a reflected detection light which is the detection light reflected off of the light spot, and generates a signal obtained through the reception of the interfering light; and
a receiving unit configured to generate, using the signal, a detection signal indicating the microscopic displacement on the surface of the examination target at the light spot, and wherein said ultrasound examination method comprises:
generating image data of the inside of the examination target, based on the detection signal indicating the microscopic displacement during a scanning operation in which the transmitting probe is kept fixed with respect to the examination target and the receiving probe is moved with respect to the examination target and the receiving probe is not in contact with the living subject.

* * * * *